(12) United States Patent
Bieberich et al.

(10) Patent No.: US 7,666,617 B2
(45) Date of Patent: Feb. 23, 2010

(54) DEVICES AND METHODS FOR PROFILING ENZYME SUBSTRATES

(75) Inventors: Charles Bieberich, Brookeville, MD (US); Xiang Li, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 69 days.

(21) Appl. No.: 12/078,157

(22) Filed: Mar. 27, 2008

(65) Prior Publication Data

US 2008/0280314 A1 Nov. 13, 2008

Related U.S. Application Data

(62) Division of application No. 11/447,089, filed on Jun. 6, 2006, now Pat. No. 7,368,258.

(60) Provisional application No. 60/687,919, filed on Jun. 6, 2005.

(51) Int. Cl.
*C12Q 1/50* (2006.01)
(52) U.S. Cl. ........................................................ 435/17
(58) Field of Classification Search ........................ None
See application file for complete search history.

(56) References Cited

U.S. PATENT DOCUMENTS

| | | | |
|---|---|---|---|
| 6,316,267 B1 | 11/2001 | Bhalgat et al. | |
| 7,033,477 B2 | 4/2006 | Alpenfels et al. | |
| 7,045,290 B2 | 5/2006 | Lindquist et al. | |
| 7,045,328 B2 | 5/2006 | Mathur | |
| 7,368,258 B1 | 5/2008 | Bieberich et al. | |

OTHER PUBLICATIONS

Ausubel, F.M., et al., "Chapter 10: Analysis of Proteins," in *Current Protocols in Molecular Biology II*, Green Publishing Associates and Wiley-Interscience (1987).
Battistutta, R., et al., "Inspecting the Structure-Activity Relationship of Protein Kinase CK2 Inhibitors Derived from Tetrabromo-Benzimidazole," *Chem. Biol.* 12:1211-1219, Elsevier Ltd. (Nov. 2005).
Berwick, D.C and Tavaré, J.M., "Identifying protein kinase substrates: hunting for the organgrinder's monkeys," *Trends Biochm. Sci.* 29:227-232, Elsevier Ltd. (May 2004).
Belz, T., et al., "In vitro assays to study protein ubiquitination in transcription," *Methods* 26:233-244, Academic Press (2002).
Blay, J-Y., et al., "Targeted cancer therapies," *Bull Cancer* 92:E13-18, John Libbey Eurotext (Feb. 2005).
Blume-Jensen, P. and Hunter, T., "Oncogenic kinase signalling," *Nature* 411:355-365, Macmillan Magazines Ltd. (2001).
Bonetta, L., "Probing the kinome," *Nat. Methods* 3:225-232, Nature Publishing Group (Mar. 2005).
Brown, M.T. and Cooper, J.A., "Regulation, substrates and functions of src," *Biochim. Biophys. Acta* 1287:121-149, Elsevier Science B.V. (1996).

Burnett, G. and Kennedy, E.P., "The enzymatic phosphorylation of proteins," *J. Biol. Chem.* 211:969-980, American Society for Biochemistry and Molecular Biology (1954).
Capdeville, R., et al., "Glivec (STI571, Imatnib), A Rationally Developed, Targeted Anticancer Drug," *Nat. Rev. Drug. Discov.* 1:493-502, Nature Publishing Group (2002).
Cohen, P. and Knebel, A., "Kestrel: a powerful method for identifying the physiological substrates of protein kinases," *Biochem. J.* 393:1-6, Biochemical Society (Jan. 2006).
Cohen, P., "The Sir Hans Krebs Medal Lecture: The role of protein phosphorylation in human health and disease," *Eur. J. Biochem.* 268:5001-5010, Blackwell Science Ltd. (2001).
Coligan, J.E., "Chapter 11: Chemical Analysis," in *Current protocols in Protein Science*, Coligan, J., et al., eds., John Wiley and Sons, New York (2003).
Courtneidge, S.A., "Isolation of novel Src substrates," *Biochem. Soc. Trans.* 31:25-28, Biochemical Society, Portland Press (2003).
Craig, R. and Beavis, R.C., "Tandem: matching proteins with tandem mass spectra," *Bioinformatics* 20:1466-1467, Oxford University Press (Feb. 2004).
Davidson, W., et al., "Discovery and characterization of a substrate selective p38α inhibitor," *Biochemistry* 43:11658-11671, American Chemical Society (Jun. 2004).
Drewes, G., "MARKing tau for tangles and toxicity," *Trends Biochem. Sci.* 29:548-555, Elsevier Trends Journals (Oct. 2004).
Dunn, B.M. "Chapter 8: Conventional Choromatographic Separation," in *Current protocols in Protein Science I*, Coligan, J., et al., eds., John Wiley and Sons, New York (Aug. 2005).
Fernando, P., et al., "Active Kinase Proteome Screening Reveals Novel Signal Complexity in Cardiomyopathy," *Mol. Cell Proteomics* 4.5:673-682, The American Society for Biochemistry and Molecular Biology, Inc. (Feb. 2005).
Fukunaga, R. and Hunter, T., "Identification of MAPK substrates by expression screening with solid-phase phosphorylation," *Methods. Mol. Biol.* 250:211-236, Humana Press (Oct. 2004).
Herbst, R.S., et al., "Gefitinib—a novel targeted approach to treating cancer," *Nat. Rev. Cancer* 4:956-965, Nature Publishing Group (Dec. 2004).
Johnson, S.A. and Hunter, T., "Kinomics: methods for deciphering the kinome," *Nat. Methods* 2:17-25, Nature Publishing Group (Jan. 2005).
Jope, R.S. and Johnson, G.V., "The glamour and gloom of glycogen synthase kinase-3," *Trends Biochem. Sci.* 29:95-102, Elsevier Ltd. (Feb. 2004).

(Continued)

*Primary Examiner*—Karen Cochrane Carlson
*Assistant Examiner*—Bin Shen
(74) *Attorney, Agent, or Firm*—Sterne, Kessler, Goldstein & Fox P.L.L.C.

(57) ABSTRACT

The present invention relates to apparatus and methods for separating and detecting enzyme substrates using separation gels. For example, the apparatus and methods can be used to separate and detect kinase substrates for further analysis. The apparatus and methods can also be used to detect enzyme inhibitors, such as kinase inhibitors.

26 Claims, 9 Drawing Sheets

OTHER PUBLICATIONS

Klein, S., et al., "Killing time for cancer cells," *Nat. Rev. Cancer* 5:573-580, Nature Publishing Group (Jul. 2005).

Knebel, A.N., et al. "A novel method to identify protein kinase substrates: eEF2 kinase is phosphorylated and inhibited by SAPK4/p38δ," *EMBO. J. 20*:4360-4369, Oxford University Press (2001).

Kolligs, F.T., et al., "Wnt/beta-catenin/tcf signaling: a critical pathway in gastrointestinal tumorigenesis," *Digestion 66*:131-144, Karger (2002).

Kumar N.V., et al., "Identifying specific kinase substrates through engineered kinases and ATP analogs," *Methods 32*:389-397, Academic Press (Apr. 2004).

Li, X., et al., "NKX3.1 Is Regulated by Protein Kinase CK2 in Prostate Tumor Cells," *Mol. Cell. Biol. 26*:3008-3017, American Society for Microbiology (Jan. 2006).

Litchfield, D.W., "Protein kinase CK2: structure, regulation and role in cellular decisions of life and death," *Biochem. J. 369*:1-15, Biochemical Society (2003).

Manning, G. et al., "The Protein Kinase Complement of the Human Genome," *Science 298*:1912-1934, American Association for the Advancement of Science (2002).

Martin, G.S., "The hunting of the src," *Nat. Rev. Mol. Cell. Biol. 2*:467-475, Macmillan Magazines Ltd (2001).

Meggio, F. and Pinna, L.A., "One-thousand-and one substrates of protein kinase CK2?," *FASEB J. 17*:349-368, The Federation (2003).

Mueller, B.K., et al., "Rho kinase, a promising drug target for neurological disorders," *Nat. Rev. Drug. Discov. 4*:387-398, Nature Pub. Group (May 2005).

Noble, M.E.M., et al., "Protein kinase inhibitors: insights into drug design from structure," *Science 303*:1800-1805, American Association for the Advancement of Science (Mar. 2004).

Osusky, M., et al., "Autophosphorylation of purified c-Src at its primary negative regulation site," *J. Biol. Chem. 270*:25729-25732, The American Society for Biochemistry and Molecular Biology, Inc. (1995).

Pagano, M.A., et al., "Protein kinase CK2: a newcomer in the 'druggable kinome'" *Biochemical Society Transactions 34*:1303-1306, Biochemical Society (Jun. 2006).

Patel, S., et al., "Glycogen synthase kinase-3 in insulin and Wnt signaling: a double-edged sword?," *Biochem. Soc. Trans. 32*:803-808, Biochemical Society (Aug. 2004).

Pelech, S., "Tracking cell signaling protein expression and phosphorylation by innovative proteomic solutions," *Curr. Pharm. Biotechnol. 5*:69-77, Bentham Science Publishers (Feb. 2004).

Pinna, L.A., "A historical view of protein kinase CK2," *Cell. Mol. Biol. Res. 40*:383-390, Elsevier Science (1994).

Reimer, U., et al., "Peptide arrays: from macro to micro," *Curr. Opin. Biotechnol. 13*:315-320, Current Biology (2002).

Ren, R., "Mechanisms of BCR-ABL in the Pathogenisis of Chronic Myelogenous Leukaemia," *Nat. Rev. Cancer 5*:172-183, Nature Publishing Group (Mar. 2005).

Sapan, C.V., et al., "Colorimetric protein assay techniques," *Biotechnol. Appl. Biochem. 29*:99-108, Portland Press Ltd. (1999).

Sarno, S., et al., "Selectivity of 4,5,6,7-tetrabromobenzotriazole, an ATP site-directed inhibitor of protein kinase CK2 ('casein kinase-2')," *FEBS Lett. 496*:44-48, Elsevier Science B.V. (2001).

Shah, K., et al., "Engineering unnatural nucleotide specificity for Rous sarcoma virus tyrosine kinase to uniquely label its direct substrates," *Proc. Natl. Acad. Sci. USA 94*:3565-3570, National Academy of Sciences (1997).

Speicher, D.W., ":Chapter 10: Electrophoresis," in *Current protocols in Protein Science II*, Coligan, J., et al., eds., John Wiley and Sons, New York (1999).

Speicher, D., "Chapter 22: Gel-Based Proteome Analysis," in *Current protocols in Protein Science III*, Coligan, J., et al., eds., John Wiley and Sons, New York (2003).

Tibes, R., et al., "Tyrosine Kinase Inhibitors and The Dawn of Molecular Cancer Therapeutics," *Annu. Rev. Pharmacol. Toxicol. 45*:357-384, Annual Reviews (Feb. 2005).

Troiani, S., et al., "Searching for Biomarkers of Aurora-A Kinase Activity: Identification of in Vitro Substrates through a Modified KESTREL Approach," *J. Proteome. Res. 4*:1296-1303, American Chemical Society (Jan. 2005).

Vandenplas, M.L., et al., "Nerve growth factor activates kinase that phosphorylate atypical protein kinase C," *Cell. Signal. 14*:359-363, Elsevier Science Inc. (2002).

Vilk, G., et al., "Inducible expressions of protein kinase CK2 in mammalian cells. Evidence for functional specialization of CK2 isoforms," *J. Biol. Chem. 274*:14406-14414, The American Society for Biochemistry and Molecular Biology, Inc (1999).

Wang, S. and Jones, K.A., "CK2 Controls the Recruitment of Wnt Regulators to Target Genes In Vivo," *Current Biology 16*: 2239-2244, Elsevier Ltd. (Nov. 2006).

Weston, C.R and Davis, R.J., "Signal transduction: signaling specificity—a complex affair," *Science 292*:2439-2440, American Association for the Advancement of Science (2001).

Wingfield, P.T., "Chapter 19: Identification of Protein Interactions," in *Current protocols in Protein Science III*, Coligan, J., et al., eds., John Wiley and Sons, New York (Aug. 2006).

Wingfield, P.T., "Chapter 20: Quantification of Protein Interactions," in *Current protocols in Protein Science III*, Coligan, J., et al., eds., John Wiley and Sons, New York (Aug. 2006).

Wooten, M.W., "In-Gel Kinase Assay as a Method to Identify Kinase Substrates," *Sci. STKE 2002*:PL15, American Association for the Advancement of Science (2002).

Yeatman, T.J., "A renaissance for SRC," *Nat. Rev. Cancer 4*:470-480, Nature Publishing Group (Jun. 2004).

Zhu, H., et al., "Analysis of yeast protein kinases using protein chips," *Nat. Genet. 26*:283-289, Nature American Inc. (2000).

Zhu, Z., et al., "Tetracycline-controlled transcriptional regulation systems: advances and application in transgenic animal modeling," *Semin. Cell. Dev. Biol. 13*:121-128, Elsevier Science Ltd. (2002).

Office Action for U.S. Appl. No. 11/447,089, Bieberich, et al., filed Jun. 6, 2006, mailed on Apr. 23, 2007.

Office Action for U.S. Appl. No. 11/447,089, Bieberich, et al., filed Jun. 6, 2006, mailed on Sep. 12, 2007.

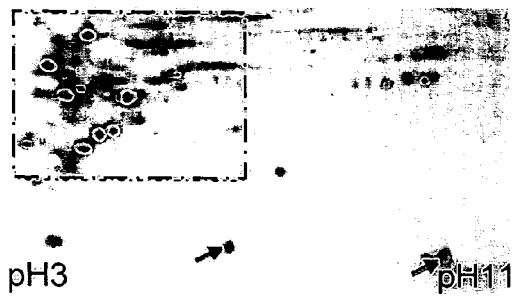
FIG.7A  FIG.7B
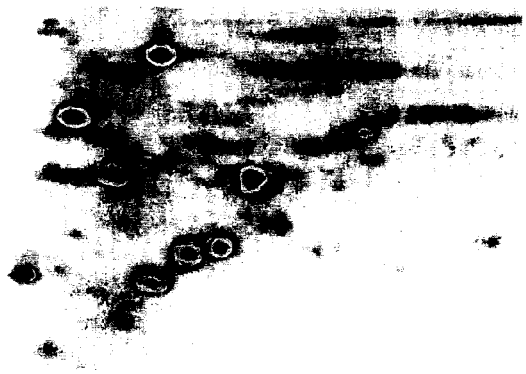
FIG.7C  FIG.7D
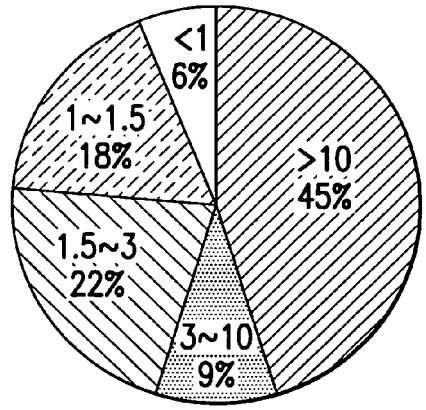
FIG.7E

DEVICES AND METHODS FOR PROFILING ENZYME SUBSTRATES

CROSS REFERENCE TO RELATED APPLICATIONS

This application is a divisional of U.S. application Ser. No. 11/447,089, filed Jun. 6, 2006 now U.S. Pat. No. 7,368,258, which claims priority to U.S. Provisional Patent Application No. 60/687,919, filed Jun. 6, 2005, the disclosures of each of which are incorporated herein by reference in their entireties.

STATEMENT REGARDING FEDERALLY SPONSORED RESEARCH

Portions of this invention may have been made with United States Government support under a grant from the United States Army Medical Research & Material Command, Grant No. DAMD-1703-1-0091. As such, the U.S. Government may have certain rights in this invention. Portions of the invention may also have been made with support from the Maryland Technology Development Corporation.

BACKGROUND OF THE INVENTION

1. Field of the Invention

The present invention relates to apparatus and methods for separating and detecting enzyme substrates using separation gels. For example, the apparatus and methods can be used to separate and detect kinase substrates for further analysis. The apparatus and methods can also be used to detect enzyme inhibitors, such as kinase inhibitors.

2. Background of the Invention

Protein phosphorylation regulates nearly all cellular processes. The enzymes that catalyze the addition of phosphate groups to proteins are termed protein kinases. Deregulated kinase activity has been linked to the pathophysiology of major diseases, including cancer, diabetes, and Alzheimer's disease (Cohen P., *Eur J Biochem* 268:5001-5010 (2001)). In recent years, kinases have become the focus of intense drug development efforts within the pharmaceutical industry. Currently, kinases are second only to G-protein coupled receptors as targets for development of therapeutics.

A major focus within the pharmaceutical industry is the identification of kinase inhibitors, as well as kinase substrates, and in general, enzyme substrates and inhibitors. The interest in identification of enzyme inhibitors has been fueled by the clinical success of several compounds with kinase inhibitory activity. A prominent example is imatinib, an ABL kinase inhibitor that is extremely effective in treating certain forms of leukemia (Ren R., *Nat. Rev. Cancer* 5:172-183 (2005)) and gastrointestinal tumors (Blay J Y, et al., *Bull Cancer* 92:E13-18 (2005)). However, wholesale inhibition of activity of certain kinases may lead to unwanted side effects. As a result, it may be desirable in many cases to block the ability of a kinase to phosphorylate a specific substrate or class of substrates. For example, in Alzheimer's disease, a kinase called GSK3 hyper-phosphorylates the protein Tau, which is a major component of the characteristic neurofibrillary tangles of Alzheimer's disease (Drewes G., *Trends Biochem. Sci.* 29:548-555 (2004). A major impediment to the development of substrate-specific inhibitors is that for most enzymes such as kinases, the spectrum of substrates that can be phosphorylated is not known. There is currently therefore a need for assays that will facilitate the identification of substrates for enzymes, and specifically kinases. The present invention fulfills these, and other, needs by providing apparatus and methods for separating, detecting and analyzing enzyme substrates, as well as methods for separating, detecting and analyzing inhibitors of enzyme activity.

SUMMARY OF THE INVENTION

In one embodiment, the present invention provides apparatus for separating an enzyme substrate from a collection of macromolecules, comprising: a separation gel; and at least one inactive enzyme that is capable of modifying the at least one enzyme substrate, wherein the enzyme is contained within the separation gel and wherein said enzyme is capable of re-activation. In additional embodiments, the apparatus can further comprise means for separating the enzyme substrate from the collection of macromolecules and means for detectibly labeling said enzyme substrate. Suitably the enzyme is a kinase.

Examples of separation gels include polyacrylamide gels. Suitable separation means include pH gradient and electrophoresis systems. Exemplary detective labeling means include a radioactive enzyme substrate label, a fluorescent enzyme substrate label, a luminescent label or a colorimetric enzyme substrate label.

In an additional embodiment, the present invention provides methods for detecting an enzyme substrate in a collection of macromolecules, comprising providing a separation gel comprising at least one inactive enzyme that is capable of modifying at least one enzyme substrate, wherein the at least one enzyme is contained within the separation gel and wherein the enzyme is capable of re-activation, loading a collection of macromolecules comprising at least one enzyme substrate into the separation gel to generate a loaded separation gel, resolving the at least one enzyme substrate on the loaded separation gel to generate a resolved separation gel, washing the resolved separation gel, incubating the resolved separation gel in a protein refolding buffer to re-activate the enzyme, incubating the resolved separation gel in an enzyme reaction buffer and detecting the at least one enzyme substrate.

In a further embodiment, the present invention provides methods for detecting a protein kinase substrate in a collection of macromolecules, comprising providing a separation gel comprising at least one inactive protein kinase contained within the separation gel, wherein the protein kinase is capable of re-activation, loading a collection of macromolecules comprising at least one protein kinase substrate into the separation gel to generate a loaded separation gel, resolving the at least one protein kinase on the loaded separation gel to generate a resolved separation gel, washing the resolved separation gel, incubating the resolved separation gel in a protein refolding buffer to re-activate the at least one kinase, incubating the resolved separation gel in a kinase reaction buffer, wherein the kinase reaction buffer comprises at least one labeled phosphate donor, thereby labeling the at least one kinase substrate and detecting the at least one labeled kinase substrate.

Exemplary phosphate donors include NTP molecules, such as a radioactively labeled NTP molecule, a fluorescently labeled NTP molecule, a luminescently labeled NTP molecule or a calorimetrically labeled NTP.

In a still further embodiment, the present invention provides methods for identifying an inhibitor of enzyme activity, comprising providing a first and a second separation gel, each of which comprises at least one inactive enzyme that is capable of modifying at least one protein, wherein the at least one enzyme is contained within each of the separation gels, and wherein the enzyme is capable of re-activation, loading a collection of macromolecules comprising at least one enzyme substrate into the first and the second protein separation gels to generate loaded separation gels, resolving the at least one enzyme substrate on the first and second loaded separation gels to generate resolved separation gels, washing the resolved separation gels, incubating the first and second resolved separation gels in a protein refolding buffer to re-activate the enzyme, incubating the first resolved separation gel in an enzyme reaction buffer, incubating the second resolved separation gel in an enzyme reaction buffer that further comprises at least one inhibitor of enzyme activity and detecting at least one enzyme substrate in the first resolved separation gel and the second resolved separation gel and comparing the first resolved separation gel and the second resolved separation gel, wherein a reduction in the detection of the at least one enzyme substrate in the second resolved separation gel indicates that enzyme activity has been inhibited. The inhibitor of enzyme activity is then identified.

The present invention also provides methods for identifying an inhibitor of enzyme activity, comprising providing a separation gel which comprises at least one inactive enzyme that is capable of modifying at least one protein, and at least one substrate for the enzyme, wherein the at least one enzyme and the at least one enzyme substrate are contained within the separation gel, and wherein the enzyme is capable of re-activation, loading a collection of macromolecules comprising at least one inhibitor of enzyme activity into the separation gel to generate a loaded separation gel, resolving at least one inhibitor of enzyme activity on the loaded separation gel to generate a resolved separation gel, washing the resolved separation gel, incubating the resolved separation gel in a protein refolding buffer to re-activate the enzyme, incubating the resolved separation gel in an enzyme reaction buffer, detecting at least one enzyme substrate in the resolved separation gel, comparing a first portion of the resolved separation gel and a second portion of resolved separation gel, wherein a localized reduction in the detection of at least one enzyme substrate in the first portion compared to the second portion indicates that enzyme activity has been inhibited, and identifying the inhibitor of enzyme activity.

Further embodiments, features, and advantages of the invention, as well as the structure and operation of the various embodiments of the invention are described in detail below with reference to accompanying drawings.

BRIEF DESCRIPTION OF THE FIGURES

The invention is described with reference to the accompanying drawings. In the drawings, like reference numbers indicate identical or functionally similar elements.

FIG. 3A-3B shows an autoradiogram of a 1D reverse in-gel kinase assay for recombinant CK2α.

FIG. 7A-7E shows CK2α RIKA of a TBB-treated LNCaP cell extract.

DETAILED DESCRIPTION OF THE INVENTION

Figure 1:
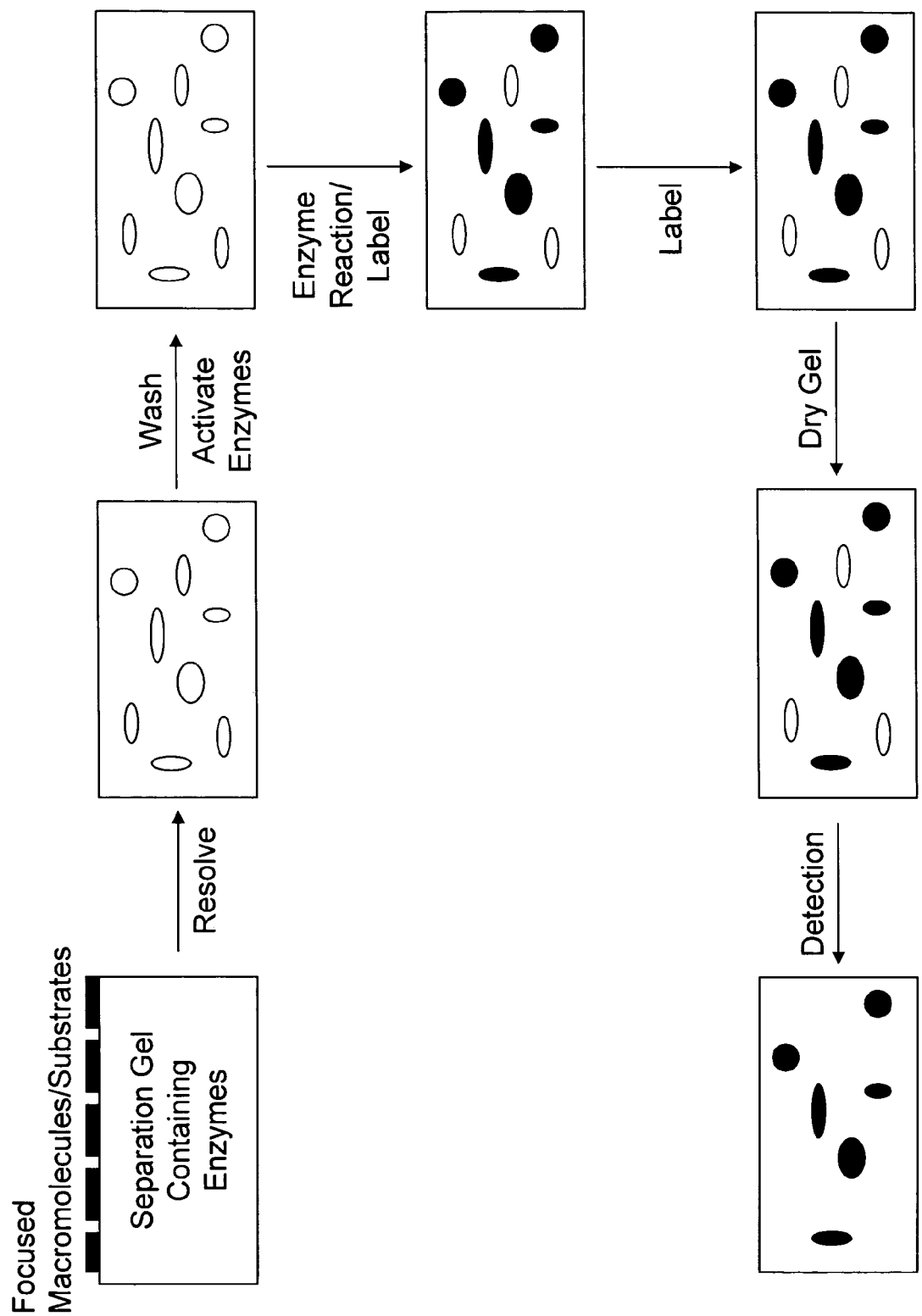
FIG. 1 is a schematic showing a method of enzyme substrate detection in accordance with one embodiment of the present invention.

It should be appreciated that the particular implementations shown and described herein are examples of the invention and are not intended to otherwise limit the scope of the present invention in any way.

In one embodiment, the present invention provides apparatus for separating an enzyme substrate from a collection of macromolecules, comprising a separation gel and at least one inactive enzyme that is capable of modifying the at least one enzyme substrate, wherein said enzyme is contained within said separation gel and wherein said enzyme is capable of re-activation. It should be understood that the term "apparatus" as used herein is the plural form of apparatus, as the present invention discloses and encompasses many apparatus. As used herein, the term "enzyme" means protein that acts as a catalyst in mediating and speeding a specific chemical (e.g., a biochemical) reaction and an "enzyme substrate" means a reactant, material or substance on which an enzyme acts. Enzyme substrates include macromolecules, which include molecules having a molecular weight in the range of a few thousand to many millions, such as, proteins, peptides, polypeptides, nucleic acids (e.g., DNA or RNA), polysaccharides (e.g., carbohydrates and sugars), lipids, etc. As used herein, the term "capable of modifying" is used to indicate that the enzyme, in its active state, modifies at least one enzyme substrate, and therefore in its inactive state, is "capable" of modifying an enzyme substrate were it to be active or activated.

In suitable embodiments, the apparatus of the present invention (as well as the methods described herein) comprise a separation gel in which an enzyme is contained. Separation gels for use in the practice of the present invention include protein separation gels as well as other macromolecular separation gels (e.g., lipid separation gels, polysaccharide separation gels). Suitably the separation gels are protein separation gels, including native protein separation gels (such as those which separate based upon the size and/or packing or folding of the protein) and denaturing protein separation gels (such as those which separate proteins with the use of charged species, thereby allowing migration via a charge/mass ratio basis). Examples of native protein (or other macromolecule) separation gels include, but are not limited to agarose gels, polyacrylamide gels, and other gels known those skilled in the art. Denaturing protein (or other macromolecule) separation gels generally require the presence of a charged buffer solution or other component to provide charge to the protein. Charged buffer solutions suitable for use in the present invention include, but are not limited to, sodium dodecyl sulfate (SDS) polyacrylamide (PA) gels and the like.

As used herein the term "contained" includes conditions in which the macromolecule or enzyme (or enzyme and enzyme substrate when analyzing inhibitors) is associated, embedded, immobilized (i.e., incapable or substantially incapable of moving in the gel), partially immobilized (i.e., capable of moving in the gel), sequestered or otherwise present in the matrix of the separation gel. The enzyme is contained such that it is present throughout the gel in a relatively uniform manner, though in other embodiments, gradients or specific concentrations of enzyme(s) can be set up within the gel. In one embodiment, separation gels for use in the practice of the present invention are prepared with enzyme in solution, such that when the gel cures or sets, the enzyme is therefore contained within and throughout the gel. In one embodiment, during the polymerization (e.g., PA) or setting process (e.g., agarose), the enzyme becomes sequestered or immobilized within the separation gel. Generally, the enzyme will be contained in the gel such that it will not migrate during separation of macromolecules during electrophoresis, but in other embodiments, the enzyme can and will move throughout the gel. In another embodiment, enzyme(s) can be added to a pre-formed separation gel either by placing a solution of enzyme on a hydrated gel and allowing the enzyme to migrate into the gel, or by de-hydrating a pre-formed gel, and then re-hydrating the gel using a solution that contains one or more enzymes (and suitably one or more chaotropic agents, such as guanidine hydrochloride, urea, formamide, etc.), thereby loading the gel with the enzyme(s) as it re-hydrates resulting in a gel that contains enzyme throughout the gel matrix.

Enzymes for use in the practice of the present invention include any enzyme that modifies (or is capable of modifying) an enzyme substrate (e.g., a protein, lipid, polysaccharide). In suitable embodiments, the enzymes are those that post-translationally modify at least one enzyme substrate, e.g., a protein. Suitable enzymes include those that modify proteins that have been either fully or partially translated. Examples of enzymes that post-translationally modify at least one protein, include, but are not limited to, protein kinases, farnesyl transferases, acetyltransferases, sulfotransferases, hydroxylases, methyltransferases, glycosyltransferases and other modifying enzymes.

The amount of enzyme to be prepared in, or added to, the separation gel is easily determined by those in this field. Suitably, the amount of enzyme contained in the separation gels of the present invention will be about 0.01 mg/ml to about 10 mg/ml (weight of protein/volume of separation gel), or about 0.1 mg/ml to about 1 mg/ml, or about 0.1 mg/ml to about 0.5 mg/ml, though larger or smaller amounts of protein can also be contained in the gel depending upon the desired application.

Separation gels for use in the practice of the present invention can contain any number of the same or different enzymes. For example, the gels can contain one type of enzyme, i.e. a particular protein kinase, several different kinds of the same type of enzyme, i.e., several different protein kinases, or several different classes of enzyme, e.g., kinases, methylransferases, etc. In one embodiment, the separation gels will contain a single type of enzyme, for example, a single type of protein kinase, within the matrix of the gel. In such embodiments, the separation gels therefore provide a platform for separation, detection and analysis of substrates for this particular enzyme, i.e., a substrates of a particular protein kinase.

Suitably, the enzyme(s) contained within the separation gel will initially be inactive. That is, they will not be capable of performing their catalytic activity without a further modification (e.g., re-folding, cleaving of a protective group, phosphorylation, glycosylation, etc.) or other activation mechanism. While in other embodiments, the enzymes contained within the separation gel can be in an active state, generally, and especially with the use of a protein de-naturation gel, the enzymes will be in an inactive state. The use of inactive enzymes allows the user to determine when and if to activate the enzymes, thereby reducing undesired enzyme activity and providing an apparatus and mechanism by which to control when activity is restored. In the case of the use of an inactive enzyme, however, the enzyme must be capable of re-activation. That is, some triggering mechanism or modification (such as re-folding) must allow the enzyme to change from its inactive state to one of catalytic enzyme activity.

In suitable embodiments, the apparatus of the present invention will further comprise a means for separating an enzyme substrate on the separation gel. A collection of macromolecules (e.g., proteins, polysaccharides, lipids) which also comprise one or more enzyme substrates for the enzyme(s) contained on the separation gel is loaded into the separation gel. The collection of macromolecules can be, for example, whole cell or whole tissue lysates, extracts from particular subcellular compartments, mixtures of synthetic or recombinant peptides, as well as natural proteins (including known and unknown proteins), or partially purified fractions, such as chromatographic fractions, of the same and other collections of macromolecules that may contain, or is known to contain, one or more enzyme substrates. After loading the collection of macromolecules into the separation gel, it is then necessary to separate the collection of macromolecules so that any potential enzyme substrates are allowed to react with the enzyme(s) contained within the separation gel. This separation step is also described herein as "resolving" the enzyme substrate on the separation gel.

Suitable means for separating the collection of macromolecules include an electrophoresis system, wherein macromolecules, e.g., proteins, are separated based upon their charge when in the presence of a charge carrying medium. Components and methods for preparing and running an electrophoresis system are well known in the art. See, e.g., Ausubel et al., *Current Protocols in Molecular Biology*, Vol II, Sec. 10, John Wiley and Sons, New York, (1987) and Coligan et al., *Current Protocols in Protein Science*, Vols. I and II, John Wiley and Sons, New York, (2002), the disclosures of each of which are incorporated herein by reference in their entireties. In embodiments where the separation gel comprises sodium dodecyl sulfate (SDS) polyacrylamide (PA), the well known gel electrophoresis (GE) system, SDS-PAGE is used. In embodiments where SDS-PAGE is used as a separation means, macromolecules, e.g., proteins are first mixed with SDS, an anionic detergent which denatures secondary and non-disulfide-linked tertiary structures, and applies a negative charge to each protein in proportion to its mass. Without SDS, different proteins with similar molecular weights would migrate differently due to differences in folding, as differences in folding patterns would cause some proteins to better fit through the gel matrix than others. The addition of SDS linearizes the proteins so that they may be separated strictly by length (primary structure, or number of amino acids). The SDS binds to the protein in a ratio of approximately 1.4 g SDS per 1.0 g protein, giving an approximately uniform mass:charge ratio for most proteins, so that the distance of migration through the gel can be assumed to be directly related to only the size of the protein.

In other embodiments, the means for separating the collection of macromolecules comprises a pH gradient, where macromolecules, e.g., proteins, are separated based upon their isoelectric point, see, Ausubel and Coligan. Isoelectric focusing a pH gradient is a method of separating proteins based on their relative content of acidic and basic residues. Macromolecules, e.g., proteins are introduced into a separation gel which has an established pH gradient (or is capable of establishing such a gradient after applying an electrical current). This gradient is established by subjecting a mixture of polyampholytes, small polymers that have different pI values, to electrophoresis before the application of the macromolecules. Proteins that have been introduced into the gel begin to move until they reach a place in the gel where the pH is equal to the isoelectric point of the protein (i.e., they are electrically neutral). Additional means for separating the macromolecules in the separation gel include other apparatus and methods are well known in the art.

In suitable embodiments, both a pH gradient and an electrophoresis system can be used to separate the enzyme substrate/macromolecules. For example, a collection of macromolecules can be loaded onto a separation gel comprising a pH gradient. The collection of macromolecules can then be focused on the separation gel using isolectric focusing as described above and in Coligan. After the macromolecules have been separated according to their isoelectric point, the macromolecules are then loaded onto a second separation gel (or in suitable embodiments, the same separation gel can be used). This loading can be accomplished either by physically removing the separated macromolecules from the gel and then loading them into the second gel (e.g., in wells as is traditionally done), or the first gel can be placed at the top of a gel electrophoresis system and the macromolecules "loaded" into the second gel via application of an electrophoretic field to drive the now-charged (e.g., after SDS denaturaition and charging) macromolecules into the gel and separate them via mass. Such separation means is commonly known as 2-dimension electrophoresis, or 2-D PAGE. See e.g, Coligan and U.S. Pat. Nos. 7,045,328; 7,045,296; and 7,033,477, the disclosures of each of which are incorporated herein by reference in their entireties.

In additional embodiments, the apparatus of the present invention further comprise means for detectibly labeling one or more enzyme substrates that are contained within the collection of macromolecules. Following separation of the macromolecules on the separation gel, it is desirable to know which, or if any, enzyme substrates were contained within the collection. After activating the enzymes originally contained within the separation gel, they will regain the ability to interact with enzyme substrates that have been separated from the collection of macromolecules. The present invention then provides means for detecting these enzyme substrates by detectibly labeling the one or more enzyme substrates on the separation gel. In suitable embodiments, the means for detectibly labeling the enzyme substrates comprises a radioactive enzyme substrate label, a fluorescent enzyme substrate label, a luminescent label or a colorimetric enzyme substrate label. Such enzyme substrate labels can be in the form of a labeled phosphate donor, a labeled protein tag, or other label that allows the enzyme substrate to be detected.

Suitable enzyme substrate labels include those described herein or otherwise well known in the art. Examples of fluorescent molecules that can be used in the enzyme substrate labels of the present invention include, but are not limited to, fluorescein, NanoOrgange®, BODIPY®, TEXAS RED® (from Invitrogen Corp., Carlsbad, Calif.), as well as other fluorescent molecules. Examples of radioactive isotopes that can be used in the enzyme substrate labels of the present invention include, but are not limited to, $^{32}P$, $^{33}P$, $^{3}H$, $^{14}C$, $^{35}S$, etc. Examples of luminescent molecules that can be used in the enzyme substrate labels of the present invention include chemiluminescent and bioluminescent molecules, such as but are not limited to, platinum luminescent molecules, SYPRO® ORANGE, RUBY and RED from Invitrogen Corp. (see, U.S. Pat. No. 6,316,267, the disclosure of which is incorporated herein by reference) and luciferase, as well as others. Examples of colorimetric assays that can be used as enzyme substrate labels of the present invention include, but are not limited to, alkaline phosphatase, Coomassie Blue G-250 dye binding (the Bradford assay), the Lowry assay, the bicinchoninic acid assay and the biuret assay (see, e.g., Sapan et al., *Biotechnol. Appl. Biochem.* 29:99-108 (1999)). Additional enzyme substrate labels can also be used in the practice of the present invention, for example, PepTag® Non-Radioactive Protein Kinase Assays (Promega, Madison, Wis.)

In another embodiment, the present invention provides methods for detecting an enzyme substrate in a collection of macromolecules, comprising providing a separation gel comprising at least one inactive enzyme that is capable of modifying at least one enzyme substrate, wherein the at least one enzyme is contained within the separation gel and wherein the enzyme is capable of re-activation, loading a collection of macromolecules comprising at least one enzyme substrate into the separation gel to generate a loaded separation gel, resolving the at least one enzyme substrate on the loaded separation gel to generate a resolved separation gel, washing the resolved separation gel, incubating the resolved separation gel in a protein refolding buffer to re-activate the enzyme, incubating the resolved separation gel in an enzyme reaction buffer and detecting the at least one enzyme substrate.

The methods of the present invention, also described herein as a Reverse In-Gel Kinase Assay (RIKA), are based upon the use of a separation gel which contains one or more enzymes within the gel. Suitably, the enzyme is inactive (i.e., not capable of catalyzing a chemical reaction), but capable of reactivation, generally by protein re-folding. Examples of enzymes suitable for use in the practice of the present invention include those described throughout, including kinases, farnesyl transferases, acetyltransferases, sulfotransferases, hydroxylases, methyltransferases, glycosyltransferases and other modifying enzymes. As noted throughout, the enzymes can be introduced into the separation gel either prior to or during formation, such that the enzyme becomes sequestered or partially immobilized during curing or gel polymerization, or the enzymes can be added after the gel has been formed, either to a hydrated or non-hydrated gel.

Once a protein separation gel is prepared, a collection of macromolecules (e.g., proteins) which comprises at least one enzyme substrate (or is thought to comprise at least one enzyme substrate) is loaded into the separation gel. Loading can occur by filling wells within the separation gel as in a traditional 1-D separation gel, or loading can comprise loading the macromolecules into a isoelectric focusing gel as described herein and known in the art.

Once the macromolecules have been loaded into the gel, the macromolecules (and hence any enzyme substrates that are present in the collection) are then resolved on the separation gel. As described herein, resolving of the macromolecule collection can occur via any mechanism or system known in the art, for example gel electrophoresis or isoelectric focusing. In suitable embodiments, isoelectric focusing is used to first focus the macromolecules via a pH gradient, and then the macromolecules are either transferred to, or further resolved on, the separation gel containing the enzyme. In suitable embodiments, the macromolecule collection is first focused using a pH gradient, and then the macromolecules are resolved on the separation gel using an electrophoresis system, i.e., what is commonly known as a 2-D gel electrophoresis separation. FIG. 1 shows a graphic representation of one embodiment of the methods of the present invention. As shown in FIG. 1, macromolecules (and hence, enzyme substrates in the collection) are first focused using a pH gradient, and then transferred to the separation gel during the resolution process, resulting in a separation gel which contains enzymes throughout the gel, and now, macromolecules, including potential or known enzyme substrates, separated throughout the gel by their mass.

In suitable embodiments of the present invention, the potential or known enzyme substrates will comprise proteins (e.g., kinase substrates or other enzyme substrates described herein), and hence, a denaturing protein separation gel will be used (though a natural separation gel can also be used). In embodiments where a collection of proteins is to be separated, an SDS-PAGE gel can be used. Following resolution, it is necessary to wash the separation gel to remove the SDS or other denaturing compound (e.g., other surfactants) prior to re-activation of the enzyme contained within the separation gel (see FIG. 1). Suitable washing buffers are well known in the art, for example, isopropanol-containing or other alcohol-containing buffers can be used.

After washing the separation gel, the activity of the enzyme must be restored. For example, if a kinase is contained within the separation gel, the ability of the kinase to phosphorylate a substrate protein must be restored. Incubating the separation gel in a protein refolding buffer restores the activity of the enzyme such that it can function as it normally would. As used herein, "incubating the separation gel" includes incubating the entire separation gel, as well as portions of the gel, either while intact or cut out/excised from the original gel. In addition, portions of the separation gel can be incubated while other portions of the gel are not. Suitably, the enzyme (e.g., kinase) and the separated macromolecules/proteins in the gel are then sequentially refolded by incubation in a refolding buffer, denatured in the presence of guanidine hydrochloride (or other suitable chaotrope), and refolded again by incubation in refolding buffer (see FIG. 1). Additional forms of restoring or reactivating the enzyme activity include, but are note limited to, cleaving a protective group, phosphorylation, glycosylation, and other methods known in the art.

As used herein with respect to restoring the activity of the enzyme contained in the separation gel, the terms "restored or reactivated" are used interchangeably to mean that the activity of the enzyme is reactivated or renewed such that the enzyme can perform its desired/required function. For example, in the case of a kinase, the activity of the kinase must be restored such that it can phosphorolate a protein by any amount.

Following re-activation of enzyme activity, the protein separation gel is incubated in an enzyme reaction buffer that allows the enzyme to perform its chemical or biochemical reaction. In the case of a kinase, the separation gel is incubated in a buffer comprising phosphate donor molecules. The separation gel can then be dried (see FIG. 1), but it is not necessary to dry the gel prior to detection. In additional embodiments, the enzyme reaction buffer can comprise at least one inhibitor of enzyme activity. In such embodiments, the methods of the present invention can be used to assay for enzyme inhibitors (as described below).

The enzyme substrate(s) are then detected on the separation gel (see FIG. 1). Suitably, the enzyme reaction buffer comprises one or more enzyme substrate labels. As described throughout, suitable enzyme substrate labels include, but are not limited to, a radioactive enzyme substrate label, a fluorescent enzyme substrate label, a luminescent enzyme substrate label and a colorimetric enzyme substrate label, as well as other labels. In additional embodiments, labeling of the enzyme substrates can occur after incubation with the enzyme reaction buffer (see FIG. 1). Such labeling can comprise labeling with a radioactive enzyme substrate label, a fluorescent enzyme substrate label, a luminescent enzyme substrate label or a calorimetric enzyme substrate label, as well as other labels and labeling methods known in the art.

Suitable detection methods include radioactive detection, fluorescence detection (e.g., using a fluorescence meter or spectrophotometer), luminescent detection, calorimetric detection, as well as other detection methods including simply the human eye.

Suitably, the enzyme substrate will be labeled with a radioactive isotope, so that detection of the enzyme substrate can be performed using various art-known methods for detecting the presence of proteins on separation gels. For example, a detection medium can be exposed to the separation gel which comprises a radioactively labeled enzyme substrate. Suitably, an x-ray film is exposed to the radioactively labeled enzyme substrate (i.e. the x-ray is placed next to or on top of the gel, see Coligan). Additional detection media include, for example, a phosphorescent plate or a gamma counter or other imaging system or device that detects radioactivity.

After the enzyme substrate has been detected, the present invention provides methods for further analysis of the substrate. For example, the enzyme substrate can be removed from the separation gel. Suitably, the enzyme substrate is physically removed from the gel by excising or cutting the substrate from the gel, and then extracting the substrate from the gel, such as by digesting the substrate in the gel with trypsin (or other protease), and then allowing the substrate to diffuse out (or be pulled out) of the gel. The enzyme substrate can also be transferred to another medium, for example, via electrophoresing the substrate out of the separation gel and onto a transfer paper, gel or simply into solution. The enzyme substrate can also be removed from the gel by de-polymerizing the gel and then removing the substrate. In other embodiments, the substrate is allowed to simply diffuse out of the gel into solution for further analysis. Other physical methods of the removing the substrate from the gel can also be used. The enzyme substrate is then analyzed to determine the composition of the substrate. For example, the enzyme substrate can be analyzed via mass spectrometry. Additional methods of analysis include those known in the art, for example, protein sequencing, antibody library matching, degradation sequence, and the like.

In an additional embodiment, the present invention provides method for detecting a protein kinase substrate in a collection of macromolecules. In this embodiment, a separation gel comprising at least one protein kinase contained within the separation gel is provided. Suitably, the protein kinase is inactive in the gel matrix, but is capable of re-activation. Suitably, a kinase of interest is obtained in a purified form, for example, by preparing a tagged version of the kinase in bacteria or in a eukaryotic protein expression system. Examples of protein kinases for use in the practice of the present invention include, but are not limited to, tyrosine kinases, serine/threonine kinases, (e.g., Aurora-A, -B and -C kinases), protein kinase CK2, mitogen-activated protein kinases, non-receptor tyrosine kinases (e.g., c-SRC and c-ABL), and the like (see, e.g., Manning, et al., "The Protein Kinase Complement of the Human Genome," *Science* 298: 1912-1934 (2002), the disclosure of which is incorporated by reference herein in its entirety). Once the kinase has been purified, it is then added to the separation gel, either prior to curing or polymerization, or during re-hydration of a dehydrated gel. In a suitable embodiment, a polyacrylamide solution is used as the separation gel, and the kinase is partially sequestered by polymerization into the gel. Suitably the separation gel is a standard denaturing SDS polyacrylamide resolving gel.

A collection of macromolecules is then loaded into the separation gel. Suitably the collection will comprise at least one protein kinase substrate. As discussed throughout, loading can comprise loading the macromolecules into wells in the separation gel, or using a pH gradient to first focus the macromolecules, followed by electrophoresing the macromolecules into the separation gen.

The protein kinase substrate (as well as the other macromolecules) are then resolved on the loaded separation gel to generate a resolved separation gel. As discussed throughout, resolving the protein kinase on the separation gel can comprise standard gel electrophoresis, isoelectric focusing, or any combination thereof, e.g., isoelectric focusing to first separate the substrates, followed by electrophoresis to resolve the proteins on the separation gel.

The separation gel is then washed to remove any denaturing buffer, such as a detergent like SDS. Suitable washing buffers include alcohol-containing buffers such as isopropanol.

The separation gel is then incubated in a protein refolding buffer to re-activate the kinase(s) that is contained in the separation gel. Suitable refolding buffers are well known in the art, for 50 mM Hepes, pH 7.6, 5 mM 2-mercaptoethanol; 50 mM Hepes, pH 7.6, 5 mM 2-mercaptoethanol, 0.05% Tween 20; 20 mM Hepes, pH7.6, 20 mM $MgCl_2$, 6 M urea. For example, the kinases contained in the separation gel and the separated proteins (including the kinase substrates) in the gel are then sequentially refolded by incubation in a refolding buffer, denatured in the presence of guanidine hydrochloride (or other suitable chaotrope), and refolded again by incubation in refolding buffer.

The resolved separation gel is then incubated in a kinase reaction buffer, wherein the kinase reaction buffer comprises at least one labeled phosphate donor, thereby labeling the at least one kinase substrate. Suitable phosphate donors include, for example any nucleoside triphosphate (NTP), such as adenosine triphosphate, guanine triphosphate, as well as nucleoside triphosphate mutants or analogs (see e.g., Shah et al., *Proc. Natl. Acad. Sci.,* 94:3565-3570 (1997), the disclosure of which is incorporated herein by reference in its entirety). It should be noted that the kinase activity (or enzyme activity in general) in the apparatus and methods of the present invention is provided by the enzyme/kinase that is contained in the separation gel, not an enzyme or kinase that is comprised within the collection of macromolecules. In other words, the enzyme activity that is being identified in the present invention comes from the enzyme that was originally contained within the separation gel prior to the introduction of any additional proteins or enzymes. Suitably the enzyme reaction buffer will comprise an enzyme substrate label, for example a radioactively labeled NTP molecule, a fluorescently labeled NTP molecule, a luminescently labeled NTP molecule or a calorimetrically labeled NTP. The enzyme substrate can also be labeled after incubation in the enzyme reaction buffer.

In suitable embodiments, the separation gel is incubated in the presence of $\gamma$-$^{32}$P-ATP or $\gamma$-$^{33}$P-ATP, which serve as phosphate group donors. After a period of incubation, the gel is washed to remove free radioactive label, and the gel is then dried (although drying the gel is not required).

The enzyme substrate is detected using a suitable method, which method will depend upon the type of label utilized. For example, if a fluorescent label is used a spectrophotometer or other fluorescence detection device can be used. If a radioactive label is used, a radioactive detection medium can be used, for example, an x-ray film, phosphorescent plate or a gamma counter or other imaging system or device that detects radioactivity. In suitable embodiments, the kinase substrates are labeled using radioactive isotopes (e.g., radioactive NTP molecules) and then exposed to X-ray film or analyzed in a phosphorimaging or similar system. Inspection of the autoradiographic film or phosphorimaging output reveals the position of proteins in the separation gel that were phosphorylated by the kinase under investigation.

As described herein, the kinase substrates can then be removed from the separation gel (e.g., via excising the substrate or transferring it to another medium) and then analyzed to determine the type and structure of the substrate. Suitable analysis techniques includes mass spectrometry, protein sequencing and antibody modeling/detection.

In one embodiment then, the present invention provides methods for detection (and eventual analysis if desired) of kinase substrates. It has been determined that incorporation of kinase(s) (or other enzymes as well) into a separation gel, such as an SDS-PAGE, does not prohibit the kinase(s) from acting on substrates that have passed through the gel during electrophoretic separation. Following re-activation of the kinase, the enzyme is able to phosphorylate substrate proteins, even though the kinase was immobilized in the gel during polymerization. The present invention therefore provides very powerful analysis apparatus and methods for determination of kinase substrates (and kinase inhibitors as discussed below).

In an additional embodiment of the present invention, prior to loading the collection of macromolecules onto the separation gel, post-translational modifications on the macromolecules (and hence, post-translational modifications on the enzyme substrates) contained within the collection are removed. For example, the collection of macromolecules can be dephosphorylated, for example using a phosphatase. In other embodiments, the collection of macromolecules (and the enzyme substrates) can be de-acetylased, de-sulfonated, de-hydroxylated, de-methylated, de-glycosylated, or any other post-translational modification can be removed prior to loading. In further embodiments, the collection of macromolecules can be acted on by an enzyme that post-translationally modifies a substrate, for example, kinases, acetyltransferases, sulfotransferases, hydroxylases, methyltransferases, glycosyltransferases, etc., prior to loading. For example, the collection of macromolecules can be "primed" with a kinase (i.e., phosphorylated prior to loading) so that an additional kinase can now act on the enzyme substrate when used in the apparatus and methods of the present invention.

As many proteins are phosphorylated (or otherwise post-translationally modified) in vivo, the macromolecule collection will often already comprise phosphorylated proteins (or other modifications) (i.e., if the macromolecule collection is a cell or tissue lysate). In embodiments of the present invention where the goal is to determine enzyme, e.g., kinase substrates, the amount of proteins that can be further phosphorylated (or otherwise post-translationally modified) using the apparatus and methods of the present invention may be less than the total population of potential substrates. By removing post-translational modifications (e.g., dephosphorylating) the collection of macromolecules prior to detection using the present invention, the complete, or nearly complete, population of potential enzyme (e.g., kinase) substrates will therefore be available for post-translational modification (e.g., phosphorylation). This will not only increase the intensity of the substrates during detection, but also potentially increase the total number of different substrates that can be detected.

In a further embodiment of the present invention, prior to collecting the macromolecules from a living system (e.g., from a cell or tissue), the organism is treated with an inhibitor of enzyme activity for the purpose of generating enzyme substrates that have not been post-translationally modified (or are reduced in post-translational modifications). For example, a cell or tissue is treated with a kinase inhibitor (including those disclosed herein or otherwise known in the art) to generate hypophosphorylated (i.e., under phosphorylated or non-phosphorylated) kinase substrates that can then be subsequently detected using the apparatus and methods of the present invention. This embodiment provides a type of check on the present invention, such that enzyme substrates that are detected using the apparatus and methods of the present invention actually do represent substrates of enzymes that are present, and acted upon by enzymes (e.g., phosphorylated), in vivo. In addition, it also provides an additional method for which enhanced detection of enzyme substrates.

In another embodiment, the present invention provides methods for identifying an inhibitor of enzyme activity, comprising providing a first and a second separation gel, each of which comprises at least one inactive enzyme that is capable of modifying at least one protein, wherein the at least one enzyme is contained within each of the separation gels, and wherein the enzyme is capable of re-activation. Suitably, the enzyme is a kinase. By utilizing two different separation gels, the effect of the inhibitor (e.g., a kinase inhibitor) can be readily determined. However, the present invention also encompasses the use of a single separation gel to screen for inhibitors of enzyme activity. As used herein, the terms "first" and "second" are not necessarily intended to refer to order. Rather, these terms are used to differentiate between two different articles, for example, two different separation gels. It is also understood that although the description of the invention refers to a first and a second, under certain embodiments, there could be a third, fourth, fifth, etc., separation gel (or other article as applicable).

Examples of inhibitors that can be identified using the apparatus and methods of the present invention include, but are not limited to small organic molecules, e.g., the present invention can be used to identify kinase inhibitors such as apigenin, diadzein, emodin, imatinib, and derivatives and variants thereof etc.

A collection of macromolecules comprising at least one enzyme substrate is then loaded into the first and the second protein separation gels to generate loaded separation gels. The collection of proteins and the enzyme substrate are then resolved on the first and the second separation gels to generate resolved separation gels. Following a wash of the gels, the first and the second gels are incubated in a protein refolding buffer to re-activate the enzyme. The first separation gel is then incubated in an enzyme reaction buffer and the second separation gel is incubated in an enzyme reaction buffer that further comprises at least one inhibitor of enzyme activity. Suitably, as discussed throughout, the enzyme reaction buffer will further comprise an enzyme substrate label, such as a radioactive label. By incubating one gel in the presence of an inhibitor (or potential inhibitor) of enzyme activity, enzyme activity will be suppressed, therefore generating a separation gel in which a reduced number of enzyme reactions have taken place. For example, in the case of a kinase/kinase substrate reaction, a kinase inhibitor will inhibit the phosphorylation of the kinase substrates, and therefore a reduced number of proteins will be labeled with the labeled phosphate donor (e.g., a radioactive NTP).

The enzyme substrates are then detected on the first and the second separation gels (e.g., by exposing the gels to an X-ray film if a radioactive label is used), and the two gels are compared, wherein a reduction in the detection of the at least one enzyme substrate in the second separation gel indicates that enzyme activity has been inhibited. As used herein a reduction in the detection includes any measurable amount of loss of signal of the label, including complete elimination of the signal. The inhibitor of enzyme activity is then identified. In embodiments where only one potential inhibitor is provided in the enzyme reaction buffer, identification of an inhibitor of enzyme activity requires only identifying the absence of enzyme activity. If multiple (i.e., 2, 5, 10, 50, 100, etc.) potential inhibitors of enzyme activity are provided, then an inhibitor can be identified by removing portions of the gel where enzyme activity was inhibited, and then digesting the substrate in the gel with trypsin (or other protease), and analyzing for the identity of the inhibitor (e.g., via mass spectrometry). The various methods of labeling, detection and resolution described throughout can also be used in the methods of identifying inhibitors of enzyme activity.

In an additional embodiment, the present invention provides methods for identifying an inhibitor of enzyme activity, comprising providing a separation gel, which comprises at least one inactive enzyme that is capable of modifying at least one protein, and at least substrate for the enzyme, wherein the at least one enzyme and the at least one enzyme substrate are contained within the separation gel, and wherein the enzyme is capable of re-activation. A collection of macromolecules comprising at least one inhibitor of enzyme activity is then loaded into the protein separation gel to generate a loaded separation gel.

The collection of macromolecules and the at least one inhibitor of enzyme activity are then resolved on the loaded separation gel. The gel is then washed and incubated in refolding buffers to re-activate the enzyme and an enzyme reaction buffers as described throughout.

The at least one enzyme substrate is then detected in the separation gel. A first portion of the resolved separation gel and a second portion of the resolved separation gel are compared, wherein a localized reduction in the detection of the at least one enzyme substrate in the first portion compared to the second portion indicates that enzyme activity has been inhibited. As used herein, a localized reduction in the detection of the enzyme substrate (i.e., a reduction in the detection of the label) includes any measurable or discernable reduction in the strength of the signal, including complete elimination of the signal, at a localized area or section of the gel. For example, in such embodiments, if a first portion of the gel shows a localized reduction in detection (i.e. a faint signal, or complete lack of signal), compared to a second portion of the gel (often a nearby section of the gel), this absence of activity indicates the presence of one or more inhibitors of enzyme activity. The inhibitor of enzyme activity is then identified.

The absence of a detectible signal, therefore, on the first portion of the gel relative to the second portion indicates that enzyme activity has been reduced or eliminated. Such an embodiment of the present invention can also be performed using two separate gels. In certain such embodiments, a second gel comprising only an enzyme can be utilized (i.e., no substrate). In other embodiments, a second gel comprising an enzyme and an enzyme substrate can be used, but where the collection of macromolecules loaded into the gel does not comprise an inhibitor. In such embodiments then, the second gel will act as a "control" gel, such that any reduction in the detection of at least one enzyme substrate in the first gel compared to the second gel will indicate the presence of an inhibitor in the first gel. The various methods of labeling, detection and resolution described throughout can also be used in the methods for screening for inhibitors of enzyme activity.

In embodiments where only one potential inhibitor is provided, identification of the inhibitor of enzyme activity requires only identifying the absence of enzyme activity. If multiple (i.e., 2, 5, 10, 50, 100, etc.) potential inhibitors of enzyme activity are provided, then the inhibitor can be identified by removing portions of the gel where enzyme activity was inhibited, and then digesting the substrate in the gel with trypsin (or other protease), and analyzing for the identity of the inhibitor (e.g., via mass spectrometry).

It will be readily apparent to those in this field that that other suitable modifications and adaptations to the methods and applications described herein can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

In-Gel Kinase Assay of CK2

CK2 regulates the half-life of the prostate-specific tumor suppressor NKX3.1 (Li, X., et al., *Mol Cell Biol*, 26:3008-3017 (2006)). Only the free monomeric form of one catalytic subunit, CK2α', is involved in regulating NKX3.1.

Purification of CK2 and Demonstration of Enzyme Activity

The protein coding regions of human CK2α gene was cloned into a protein expression vector to produce the protein in *E. coli*. A CK2α kinase activity-deficient mutant was also generated in parallel. CK2α was expressed in *E. coli* and partially purified by nickel resin chromatography. To confirm that the recombinant CK2α possessed kinase activity that could be manifested after electrophoresis in a denaturing polyacrylamide gel, an in-gel kinase assay was performed on the partially purified CK2α with casein as a substrate in the gel. Standard conditions for SDS removal (i.e., alcohol-comprising buffer), protein refolding, and a kinase reaction were used. An exemplary protocol for protein re-folding is represented below:

Buffers:

A. Renaturing solution 1: 50 mM Hepes, pH 7.6; 5 mM 2-mercaptoethanol

B. Renaturing solution 2: 50 mM Hepes, pH 7.6; 5 mM 2-mercaptoethanol, 0.05% Tween 20

C. Denaturing solution: 20 mM Hepes, pH 7.6; 20 mM $MgCl_2$, 6 M urea

Protein Refolding

1. Wash the gel in 200 mls of 20% isopropanol, 50 mM HEPES twice, each for 30 minutes with shaking. The second wash can be done at 4° C. over night.

2. Wash the gel in 200 mls of renaturing buffer1 twice, each 30 minutes with shaking.

3. Wash the gel in 200 mls of denaturing buffer twice, each 15 minutes with shaking. Keep the gel in the second denaturing buffer.

4. Transfer the gel from room temperature to 4° C. Add 200 mls of renaturing buffer2 with 0.1% tween 20 to the second 200 mls of denaturing buffer and shake the gel for 15 minutes.

5. Remove 200 mls of buffer from the container and add 200 mls of fresh renaturing buffer2.

6. Repeat step 5 twice.

7. Wash the gel with 200 mls of renaturing buffer2.

8. Repeat step 7 twice.

9. Add remaining 400 mls of fresh renaturing buffer2 and incubate with shaking at 4° C. overnight.

Figure 2A:
FIG. 2A-2B shows an autoradiogram of an in-gel kinase assay for CK2α.
Figure 2B:

A parallel gel with no protein as substrate was run as a negative control. The activity of as little as 0.5 ng of CK2α electrophoresed in the gel could readily be detected by an in-gel kinase assay (FIG. 2). Although a low degree of autophosphorylation by CK2α was apparent when higher quantities of CK2α were present (FIG. 2), the signal was consistently >50-fold higher in the presence of casein. These results demonstrated that the recombinant CK2α expressed in *E. coli* could be correctly refolded and regain its catalytic activity after denaturing SDS-PAGE under reducing conditions. In FIGS. 2A and 2B, 5, 2.5, 0.5, 0.05, 0.005 and 0.0005 µg recombinant CK2α were loaded in lanes 1-6 respectively in a gel co-polymerized with 0.5 mg/ml of casein (FIG. 2A) or a gel with no protein (FIG. 2B). The signal in FIG. 2B is due to autophosphorylation by CK2α.

Demonstrating Activity of CK2α in a One-Dimensional RIKA Using Casein as a Model Substrate To establish an assay capable of profiling kinase substrates, a polyacrylamide gel in which a kinase was partially immobilized throughout the gel during polymerization was generated. In essence, this procedure is the reverse of a canonical in-gel kinase assay, where the substrate is immobilized and the kinase is mobile in the electric field.

Figures 3A, 3B:
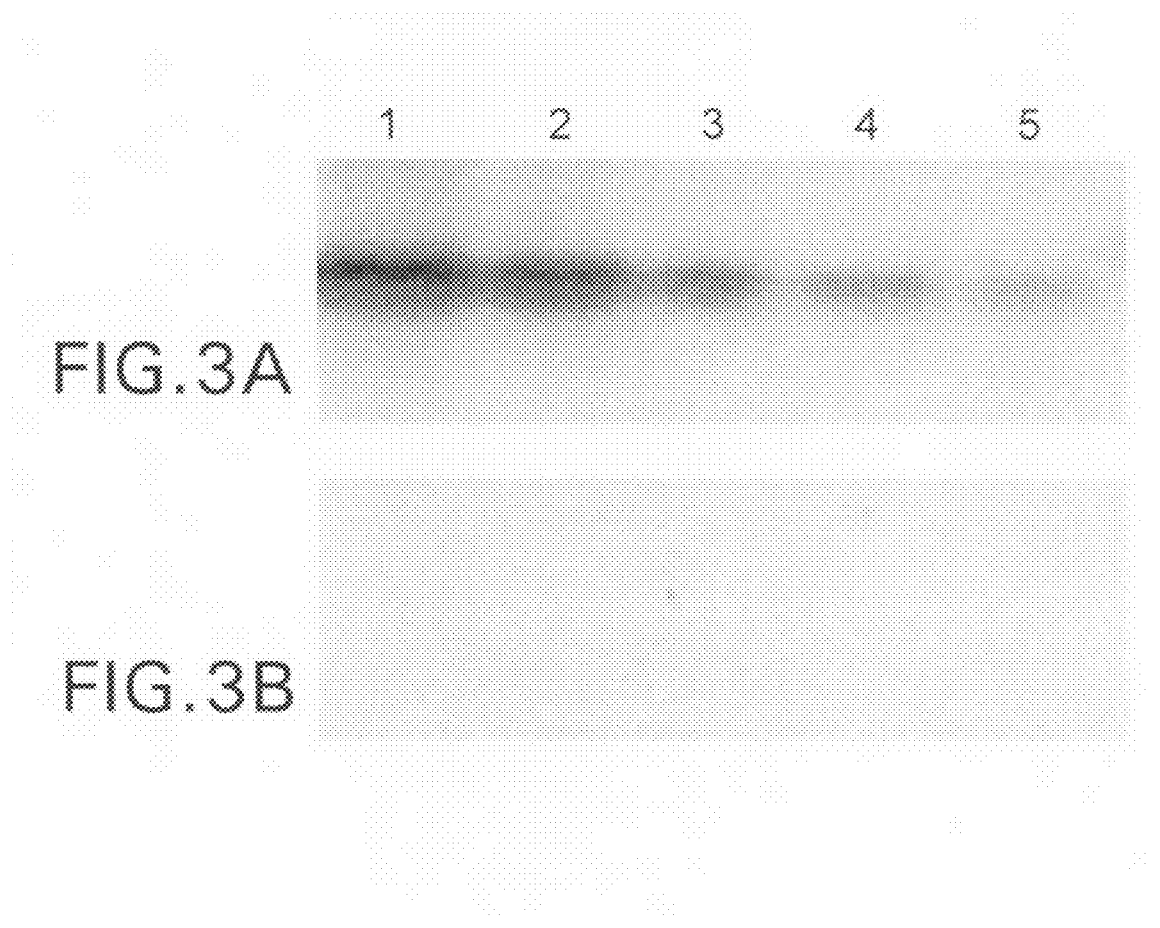

To determine whether recombinant CK2α was active in a RIKA, an assay was performed with 0.1 mg/ml of CK2α evenly distributed in a 12% polyacrylamide gel. A parallel assay was performed with 0.1 mg/ml of kinase activity-deficient mutant CK2α present in the gel. Varying amounts of casein ranging from 5 µg to 0.1 µg were electrophoresed through the kinase-laden gels. Gels were subsequently processed using a standard in-gel kinase assay protocol for SDS removal, protein refolding and kinase reaction in the presence of $\gamma$-$^{32}$P-ATP and exposed to X-ray film. Examination of the autoradiogram resulting from a 15-minute exposure of the gels revealed clear evidence of CK2α phosphorylation of casein in all lanes in a mass-dependent manner (FIG. 3A). In contrast, no detectable phosphorylation signal was observed in the kinase activity-deficient mutant gel (FIG. 3B). These data clearly demonstrated that CK2α immobilized in the polyacrylamide gel was capable of phosphorylating casein. That the assay was capable of detecting 100 ng of casein in a 15-minute exposure indicated it might be possible to detect picomole and perhaps sub-picomole quantities of proteins with longer exposures. In FIGS. 3A-3B, 5, 2.5, 1, 0.2, 0.1 µg casein were loaded in lanes 1-5 respectively in a gel co-polymerized with 0.1 mg/ml CK2α (FIG. 3A) or a gel co-polymerized with 0.1 mg/ml kinase activity-deficient CK2α mutant (FIG. 3B).

Two-Dimensional RIKA for CK2α

300 µg of protein lysate from LNCaP cells was applied to a 17 cm, pH 3-10 Immobilized pH Gradient (IPG) strip. After isoelectric focusing (IEF), the strip was electrophoresed on an SDS-PAGE gel containing 0.1 mg/ml of CK2α evenly distributed in the gel. The gel was then carried through an in-gel kinase assay procedure to allow CK2α to phosphorylate its substrates present in the LNCaP lysates. A parallel assay was performed with the kinase activity-deficient CK2α mutant at the same concentration in the gel as a negative control.

Figure 4B:
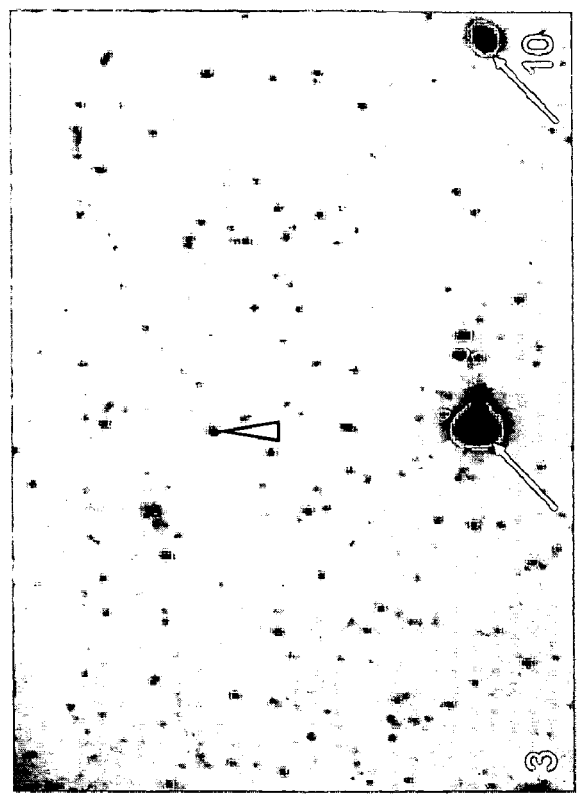
FIG. 4A-4B shows an autoradiogram of a 2D reverse in-gel kinase assay for CK2α.
Figure 4A:

As shown in FIG. 4A, greater than 50 distinct isotopically labeled spots were apparent in the autoradiogram of the gel containing active CK2α, and the signal was distributed over a wide molecular weight and pH range. The sharp speckled signal was not reproducible and varied with each experiment and was therefore considered to be background. In contrast, the pattern of diffuse signal was highly reproducible. Interestingly, the density of labeled spots was higher in the low pH range, although by silver staining of a parallel gel without kinase, the majority of proteins were distributed in the high pH range. It is important to note that overlaying RIKA films with silver stained parallel gels (without CK2α) revealed some autoradiographic signal that did not correspond to spots on the silver stained gel. These data suggest that the CK2α RIKA may be capable of detecting sub-picomole quantities of certain proteins.

Several radiolabeled spots were also apparent on the negative control gel containing kinase activity-deficient CK2α (FIG. 4B). These spots most likely represent various kinase activities present in the LNCaP extract. The two strongly labeled low molecular weight spots most likely represent autophosphorylation of the nucleotide diphosphate kinases NM23 H1 and H2. LNCaP whole cell extracts were separated in the first dimension using pH 3-10 IPG strips, then in the second dimension by SDS-PAGE on a gel cast with 0.1 mg/ml recombinant CK2α (FIG. 4A), or a gel cast with 0.1 mg/ml kinase activity-deficient CK2α mutant (FIG. 4B). The PAGE gels were then processed for 2D RIKA. Arrow, autophosphorylation of NM23 H1 & H2; Arrowhead, examples of sharp speckled background signal.

Figure 5B:
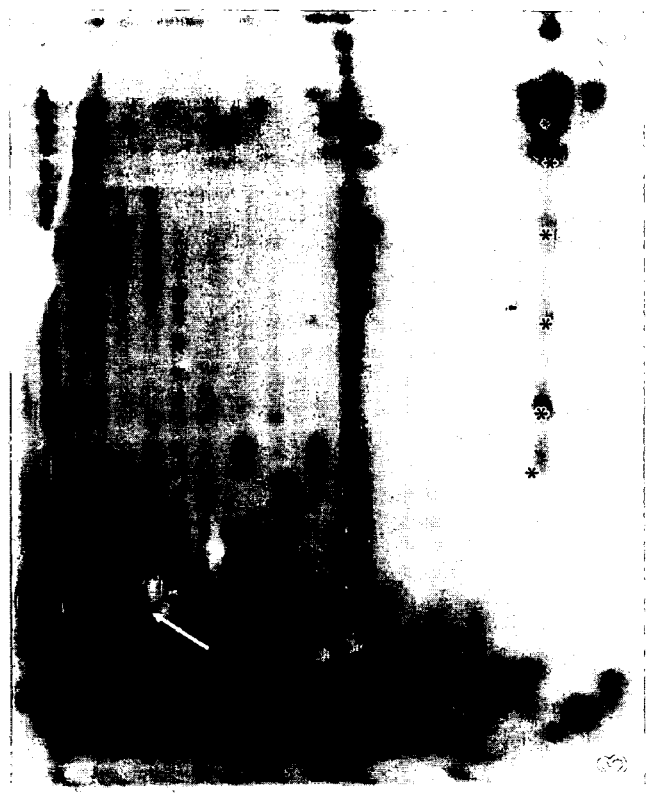
FIG. 5A-5B shows an autoradiogram of 2D reverse in-gel kinase assay for CK2α and CK2α'.
Figure 5A:

Proteins present in the LNCaP cell extract are clearly phosphorylated by CK2α immobilized in a polyacrylamide RIKA gel, and their positions are easily revealed by autoradiography. Additional 2D RIKAs with various concentrations of CK2α ranging from 1 to 100 μg/ml were also performed, and the results demonstrated that the substrate profile revealed by the assay was highly reproducible and did not change as kinase concentration in the gel was altered. A similar series of experiments was performed with recombinant CK2α', which, although it is also a catalytic CK2 subunit, is a distinct kinase encoded by a different gene. Comparison of the RIKA profile of substrates for CK2α and CK2α' revealed extensive overlap, however potential substrates that were uniquely or preferentially phosphorylated by each kinase were observed (FIGS. 5A-5B). Using the same protocol and reagents, the results of 2D RIKAs are highly reproducible. The differences in signal pattern between FIGS. 4A-4B and 5A-5B are due to the use of different 2D rehydration buffer recipes and different pH range IPG strips. 0.1 mg/ml of CK2α (FIG. 5A) and CK2α' (FIG. 5B) were co-polymerized in the gels. Arrows, representative protein substrate specific for CK2α; Asterisks, proteins preferentially phosphorylated by CK2α'. IPG strips used were pH 3-11.

In an initial attempt to identify substrates of CK2α by RIKA, the LNCaP cell extract was fractionated on a mono-Q anion exchange column to reduce sample complexity. Samples from a single fraction were processed for 2D RIKA for CK2α. Autoradiography revealed 12 potential substrates with various signal intensities. Three spots with relatively intense signals were excised from the RIKA gel and sent for protein identification by mass spectrometry-based peptide sequencing (Protana, Inc.). Peptide sequencing identified CK2α as one component of all three spots. Another component of one spot was identified as Nucleophosmin/B23 and two other spots were determined to also contain distinct isoforms of Nucleolin (Protein C23).

Phosphatase Treatment Broadly Increases RIKA Labeling.

Figure 6A:
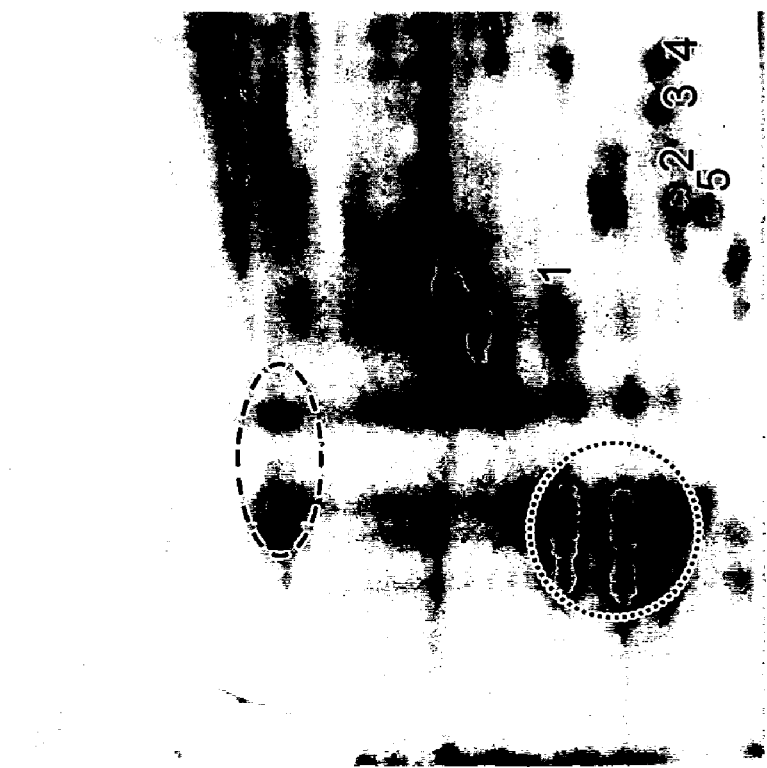
FIG. 6A-6B shows a CK2α RIKA for phosphatase-treated LNCaP lysates.
Figure 6B:
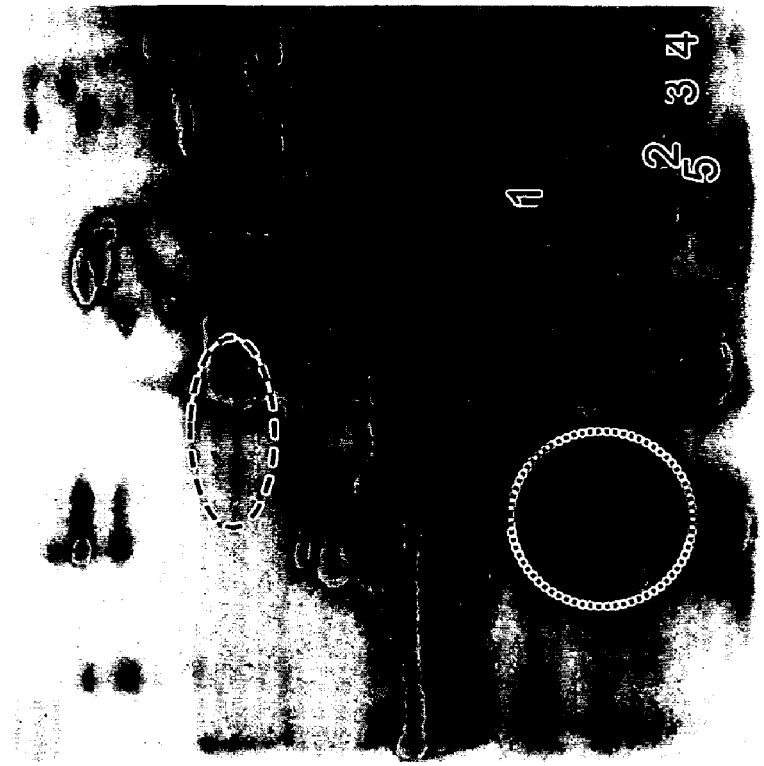

It is axiomatic that that a portion of the pool of most physiologic substrates should be phosphorylated in vivo when the kinase is active. It follows then, that removal of phosphate groups from true substrates would increase the concentration of molecules available to be phosphorylated. To determine the effect of in vitro phosphatase treatment, an aliquot of an LNCaP lysate anion exchange fraction was treated with λ phosphatase and analyzed by CK2 RIKA. Comparison of the RIKA signal obtained with and without phosphatase treatment revealed a dramatic increase in signal intensity in the vast majority of spots (FIGS. 6A-6B and Table 1). Together, these data strongly suggest that most of the proteins detected by the CK2 RIKA existed as phosphoproteins in vivo. FIGS. 6A-6B, LNCaP cell lysates were fractionated by Mono Q ion-exchange chromatography. Aliquots (300 μg) of one fraction were treated with bacteriophage λ phosphatase at 30° C. for one hour or left untreated. The lysates were then TCA-precipitated and applied to a 2D RIKA gel containing 25 μg/ml recombinant CK2α. RIKA autoradiograms from the control sample (FIG. 6A) and phosphatase-treated sample (FIG. 6B) are shown. Numbers (1-5) represent the matched pairs of spots present on both gels. Spots in the circles on the control gel collapsed into single spots due to basic shifts in pI after the removal of phosphate groups. Left sides of each panel are acidic.

TABLE 1

| Spot ID | Signal Quantity (Arbitrary Unit) | | Ratio |
|---|---|---|---|
| | Control | Phophatase treated | |
| 1 | 2683 | 41381 | 15.4 |
| 2 | 2317 | 2502 | 1.1 |
| 3 | 2575 | 48507 | 18.8 |
| 4 | 3399 | 38153 | 11.2 |
| 5 | 3397 | 2769 | 0.8 |

Inhibition of CK2 In Vivo Increases Signal Intensity in a CK2 RIKA.

Inhibition in cells was reasoned to increase the concentration of non-phosphorylated forms of true CK2 substrates, leading to a greater signal intensity in a RIKA. LNCaP cells were treated for 30 minutes with 4,5,6,7 tetrabromobenzotriazole (TBB), a potent and highly selective CK2 inhibitor. Whole cell extracts of TBB-treated and control vehicle-treated cells were analyzed in parallel by a CK2 RIKA. The data shown in FIGS. 7A-7E demonstrate that the intensity of labeling for most of the proteins detected in the CK2 RIKA increased when CK2 was inhibited in vivo. Moreover, new spots appeared after CK2 inhibition (FIGS. 7A-7E). FIGS. 7A-7E, LNCaP cells at 80% confluence were treated with 100 μM TBB or vehicle (DMSO). 300 μgs of a whole cell lysate from each treatment were applied to a 2D RIKA containing 25 μg/ml recombinant CK2α. FIG. 7A is an autoradiogram of a RIKA from the vehicle-treated LNCaP cell lysate. FIG. 7B is an autoradiogram of the TBB-treated LNCaP cell lysate. FIG. 7C is the inset in FIG. 7A. FIG. 7D, is the inset in FIG. 7B. FIG. 7E is a pie chart showing the ratios of signal intensities of matched pairs of spots on TBB-treated and control gels. The signal intensities were quantified using the Z3 2D-PAGE analysis system (Compugen). Arrows on each autoradiogram designate the endogenous kinase activities of NM23 H1 & H2 and serve as an internal control. Arrowheads show representative signals present only in the TBB-treated sample.

Figure 8B:
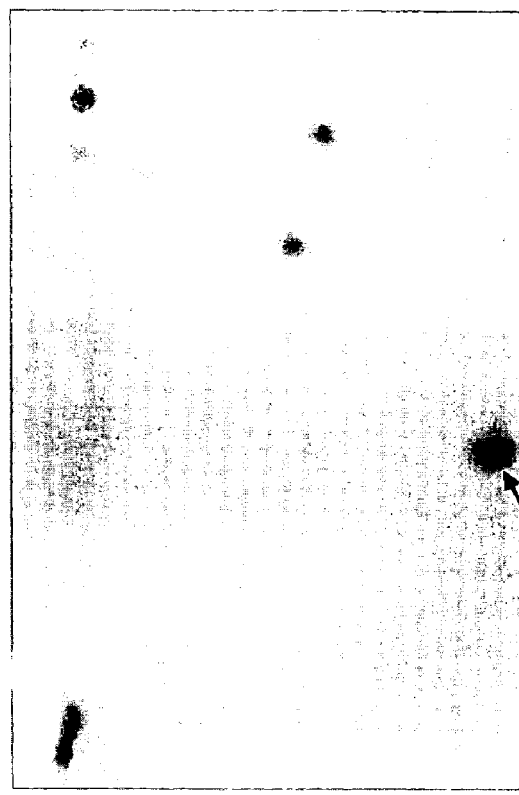
FIG. 8A-8B shows PKA RIKA for a TBB-treated LNCaP cell extract.
Figure 8A:
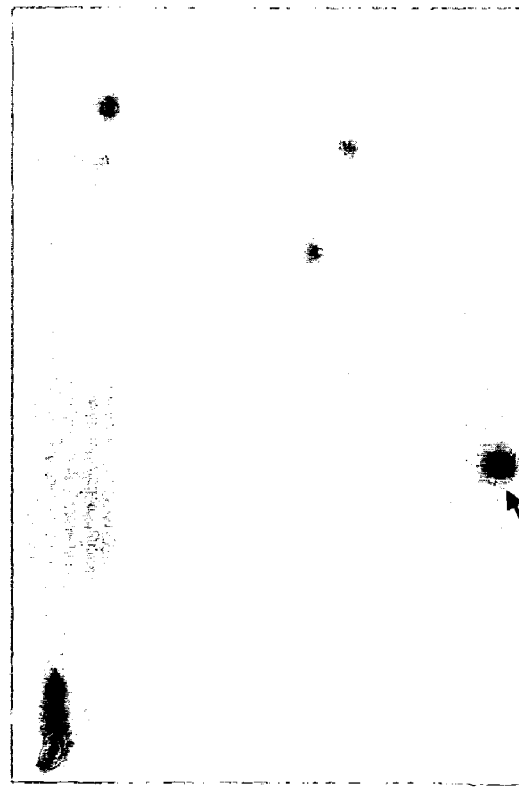

These data strongly suggest that most of the proteins labeled in a CK2 RIKA became de-phosphorylated upon CK2 inhibition in vivo. These data are consistent with the interpretation that the majority of the proteins labeled in a CK2 RIKA are true physiologic substrates of this kinase. To demonstrate that the effect was not due to a non-specific effect of TBB, for example, a global stimulation of phosphatase activity, a RIKA was performed with Protein Kinase A (PKA) on phosphatase-treated and untreated samples of the same LNCaP fraction analyzed in FIGS. 7A-7E. No increase in signal intensity in the TBB-treated extract was observed for any of the proteins detected, demonstrating that the effect of TBB was specific for CK2 RIKA substrates (FIG. 8A-8B). These data also demonstrate that PKA is also active in a RIKA. It is also important to note that PKA detected many fewer proteins (FIGS. 8A-8B). This is consistent with the fact that PKA has only 25 known substrates, whereas CK2 has more than 300.

Identification of Putative CK2 Substrates by LC-MS/MS

To identify substrates of CK2α by RIKA, the LNCaP cell extract was fractionated on a mono-Q anion exchange column to reduce sample complexity. Samples from several fraction were processed for 2D RIKA with CK2α. Autoradiography revealed multiple potential substrates with various signal intensities. Spots with relatively intense signals were excised from the RIKA gel and analyzed for protein identification by mass spectrometry-based peptide sequencing. Peptide sequencing identified CK2α as one component of all spots. Using the pI and molecular weights estimated from the 2D gel analysis in conjunction with analysis of the mass spectra with X!-tandem resulted in protein identification with a high degree of confidence. The identities of the proteins are listed in Table 2. FIG. 8A-8B, an equivalent mass of protein used for the RIKA shown in FIGS. 7A-7E was applied to a RIKA gel containing 50 µg/ml recombinant PKA. Arrows designates the activity of the endogenous kinase NM23 H1 which serves as an internal control. FIG. 8A is an autoradiogram of the PKA RIKA using the vehicle-treated lysates. FIG. 8B is an autoradiogram of the RIKA using the TBB-treated lysates.

TABLE 2

| Protein | Peptides matched | Sequence Coverage | Predicted Mass (kDa)/pI | Known CK2 substrate? |
|---|---|---|---|---|
| Annexin A4 | 14 | 50% | 35.8/5.9 | Yes |
| Nucleophosmin (B23) | 5 | 23% | 28.5/4.6 | Yes |
| Nucleolin (C23) | 21 | 21% | 76.4/4.6 | Yes |
| Glucose-regulated protein (GRP94) | 54 | 46% | 92.4/4.8 | Yes |
| Tumor rejection antigen (Gp96) 1 variant | 16 | 28% | 66.0/5.1 | Yes |
| Heterogeneous nuclear ribonucleoprotein (HnRNP) C | 9 | 23% | 25.2/5.0 | Yes |
| Prostaglandin E synthase 3 | 6 | 37% | 18.7/4.4 | No |

Table 2. Summary of proteins identified by LC-MS/MS from CK2 RIKA gels. Spots matching signals on RIKA gels were excised, digested by trypsin, and processed for LC-MS/MS. The MS/MS mass spectra were searched against the NCBI non-redundant protein database using the X!-tandem algorithm (thegpm.org). Identifications were considered positive if the protein probability score was P<0.01 and consistent with the observed molecular weight and pI.

Apigenin Inhibits CK2α Activity in a Reverse in-Gel Kinase Assay.

Figure 9:
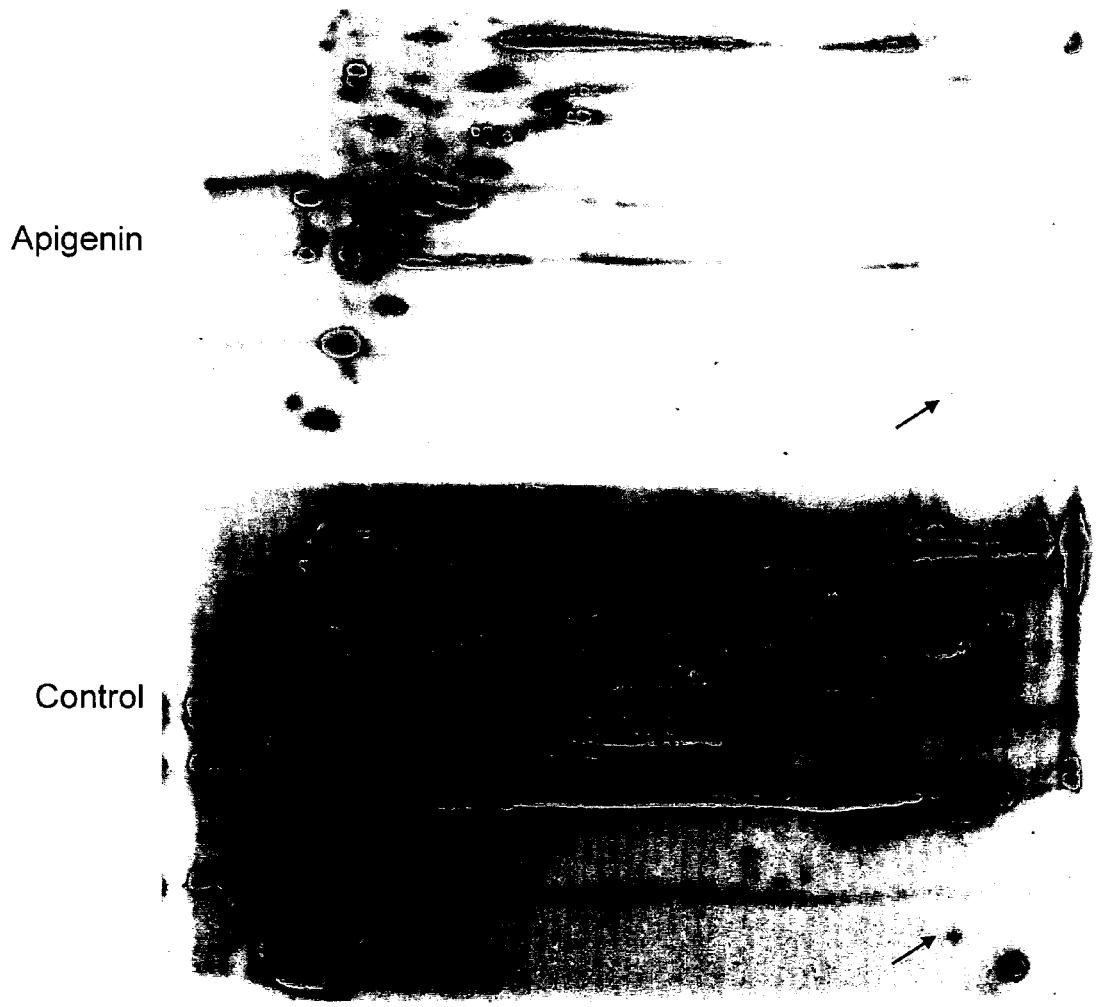
FIG. 9 shows inhibition of CK2α kinase activity in a RIKA.

300 µg of LNCaP lysate was treated with bacteriophage λ phosphatase at 30° C. for 1 hour. The lysate was then precipitated with TCA, resolublized in IEF rehydration buffer and applied to CKα reverse in-gel kinase assay with 25 µg of recombinant human CK2α cast in the gel. 75 µM apigenin was added in the reverse in-gel kinase assay buffer and a parallel assay was performed with same volume of vehicle (DMSO) added to the reaction buffer. Arrow in FIG. 9 denotes the position of the endogenous kinase NM23 which serves as an internal control that is not affected by apigenin treatment.

Example 2

Detection of CK2 Substrates in an LNCaP Cell Extract by 1D RIKA and KESTREL

To compare the extent to which RIKA and Kinase Substrate Tracking and Elucidation System (KESTREL) are capable of detecting potential substrates, a whole cell lysate from LNCaP cells (50 mgs protein) will be fractionated by anion exchange chromatography and eluted with a NaCl step gradient into 40 fractions. Equivalent volumes of the load, flow and elution fractions will then be analyzed in the RIKA and KESTREL analyses. To perform 1D CK2 RIKAs, two aliquots of each fraction will be treated with λ phosphatase and electrophoresed through denaturing acrylamide gels containing either 10 ug/ml active or kinase-dead CK2λ. After electrophoretic resolution of proteins on the RIKA gel, SDS will be removed by incubation in 20% isopropanol. The gels will then be carried through a series of buffer changes to refold the proteins present in the gel and to restore the catalytic activity of CK2α. A kinase reaction will be performed in the presence of $\gamma$-$^{32}$P-ATP, and unreacted $\gamma$-$^{32}$P-ATP will be removed by extensive washing. The gel will be dried and exposed to X-ray film to produce an autoradiogram.

To prepare samples for KESTREL, aliquots of the anion exchange load, flow, and elution fractions will be dialyzed against kinase buffer containing either Mg2+ or Mn2+. An amount of protein equivalent to that analyzed by RIKA will be reacted with CK2α in the presence of $\gamma$-$^{32}$P-ATP and resolved by standard PAGE. The Mg2+ and Mn2+ reactions will be analyzed on separate gels in parallel with mock CK2α reactions that serve as controls for endogenous kinase activity. Autoradiograms of dried KESTREL gels will be obtained for comparison to RIKA autoradiograms.

Analysis of 1D RIKA and KESTREL autoradiograms from equivalent masses of protein from each fraction will provide a low-resolution comparison of the detection capabilities of the two methods and will reveal fractions that are relatively rich in potential CK2 substrates.

Detection of CK2 Substrates in LNCaP Cell Extract Fractions by 2D RIKA and KESTREL Fractions identified to be relatively rich in CK2 substrates will be analyzed by 2D RIKAs and by standard 2D gel analysis after the KESTREL kinase reaction. Based on the 1D KESTREL results, either the Mg2+ or Mn$^{2+}$ reaction condition will be chosen, depending on which yields a better signal-to-noise ratio. RIKA and KESTREL autoradiograms will be quantitatively compared using the Compugen Z3 2D-gel analysis software package to align the gels, and to generate relative signal intensity data for each matched pair of spots. Based on these data, it will be possible to quantitatively determine the sensitivity of each method for spot detection starting from an equivalent mass of protein. Spots that are detected exclusively by one or the other method will also be revealed as unmatched spots in the Z3 analyses.

Reproducibility of 2D RIKA Gels

The fact that the RIKA requires in-gel polymerization, denaturation, and re-folding of the kinase under investigation raises questions regarding gel-to-gel variability. These variables are layered on top of the standard reproducibility issues inherent in all 2D proteomic analyses. To quantify the extent of gel-to-gel variability in substrate detection in 2D RIKAs, equivalent aliquots of LNCaP fractions will be analyzed by a 2D CK2 RIKA on consecutive days. At least three independent fractions will be assayed. The resulting autoradiograms will be quantitatively analyzed using the Z3 software for alignment and spot matching, and to generate relative intensity data.

Expected Results

Given the potential advantages of the RIKA in terms of background reduction as well as kinase reaction time and conditions, this assay will be considerably more sensitive than KESTREL in detecting substrates present within fractionated cell extracts. Both methods will detect essentially the same pool of substrates. However, it is possible that significant differences in the substrate spectrum may be revealed. For example, incomplete re-folding of substrates in the RIKA may permit phosphorylation of substrates on non-physiologic sites. Conversely, KESTREL may permit phosphorylation of proteins that can only be recognized by CK2 as part of a protein complex. Regarding gel-to-gel variability of 2D RIKAs, >90% reproducibility is anticipated. As an alternative method of data analysis, it is possible to quantitatively compare RIKA gels using a phosphorimager. Taking this approach would obviate potential concerns over the non-linearity of X-ray film under some exposure conditions. However, this method would require spot matching to by performed by hand.

Example 3

Validation the RIKA by Demonstrating its Ability to Detect Known CK2 Substrates and to Discover Previously Unknown Substrates Mass Spectrometric Identification of Potential CK2α Substrates Revealed by RIKA.

Since the total number of true CK2 targets in human cells is unknown, it is difficult to derive a statistical argument to determine how many identifications should be performed to achieve a given degree of confidence. It is anticipated that by characterizing 80-100, likely both known and unknown potential substrates will be encountered. To achieve this goal, a series of 2D CK2α RIKAs will be performed using fractionated LNCaP extracts as a source of potential CK2α substrates Aliquots of anion exchange fractions of LNCaP whole cell lysates will be focused on 18 cm linear IPG strips with a pH range of 3-6, 5-8, 7-9, and 3-10. Preliminary studies using pH 3-10 IPG strips demonstrated that the majority of potential targets lie within the range of pH 3-5. It is anticipated that extending the 3-5 pH range over a distance of 18 cm will significantly improve resolution in this range. Although a minority of potential targets lie within the 7-10 pH range, it will be important to include these proteins in the analyses as well. Second dimension 12% polyacrylamide gels containing 10 µg/ml CK2α will be prepared and loaded with focused IPG strips. The RIKAs will be performed as described herein.

Since the spots from RIKA gels contain protein mixtures including the kinase and its potential substrates, it is proposed to identify the substrates by peptide sequencing based on LC-MS/MS. Tryptic peptide mixtures will be separated by reverse-phase HPLC followed by analysis on a Thermo Finnegan LCQ Deca XP ion trap mass spectrometer. The resulting full scan mass spectra will be analyzed using the TurboSequest algorithm in the Bioworks 3.1 software package (Thermo Finnegan). The identity of proteins present in each spot based on the mass spec data in conjunction with the pIs and molecular weights estimated on 2D gels will be determined. In addition, the spectra will be analyzed to determine whether phosphorylation sites can be revealed.

Partial Validation of Potentially Novel Substrates.

Six criteria have been suggested to formally and stringently identify a novel protein kinase substrate Berwick, D. C. and J. M. Tavare, Trends Biochem. Sci. 29:227-232 (2004). Based on meeting all of these criteria, only a small number of proteins can be considered bona fide targets of CK2.

The amino acid sequence of novel potential substrates will be screened for the presence of the minimum potential CK2 phosphorylation site T/S-x-x-E/D. Those without a site will be considered to be false positives.

Proteins containing a minimal CK2 consensus motif will be characterized further using in vitro kinase assays. Full-length cDNA clones coding for potential substrates will be obtained from public repositories or commercial suppliers. His-tagged versions of potential substrates will be produced in bacteria and partially purified by nickel chromatography. In vitro kinase reactions will be performed to determine if the candidate can be phosphorylated by purified CK2α. Those that can will be further characterized to determine the stoichiometry of phosphorylation. Substrates with significant stoichiometry will be considered level ii-validated candidates.

In anticipation of a final validation step, MALDI-TOF MS will be performed on in vitro phosphorylated substrates to determine the site(s) of phosphorylation by post-source decay. For a minimum of 2 novel putative substrates, a rabbit anti-phosphopeptide polyclonal antisera will be derived directed at the putative CK2 site through a commercial antibody production service (Covance). Sera from production bleeds will then be used to probe Western blots of TBB-treated and control cells. If CK2 inhibition by TBB diminishes the extent of in vivo phosphorylation, then the protein will be considered a bona fide CK2 target.

Example 4

Developing a RIKA to Profile Substrates of a Non-Receptor Tyrosine Kinase

Of the more than 500 known or suspected human kinases, 38 are non-receptor tyrosine kinases. They include canonical oncoproteins, for example c-SRC and c-ABL, whose activated forms have been causally linked to multiple cancers. Through the use of anti-phosphotyrosine antibodies and other approaches, an extensive list of SRC substrates has been defined, however it is likely that this list is incomplete. RIKA will enable the identification of potential physiologic c-SRC substrates. The logic of choosing SRC as a model non-receptor tyrosine kinase parallels that for choosing CK2 as a model serine/threonine kinase: the database of known and suspected substrates will be valuable to establish the validity and utility of the assay. The rate of correct in-gel refolding will be enhanced by employing a recently-developed strategy that takes advantage of the chaperone-like function of SUMO, Kurepa, J., et al., J Biol Chem. 278:6862-6872 (2003). The presence of the SUMO domain will facilitate in-gel SRC refolding and enable the successful development of a model RIKA for non-receptor tyrosine kinases.

Generation of a SUMO-SRC Fusion Protein and Determination of Activity

A SUMO-SRC fusion protein will be created using the SUMOpro Expression System (LifeSensors, Inc.). The coding region of a constitutively active c-SRC mutant (Y530F) will be cloned into pSUMO and transformed into BL21 (DE3) cells for protein production. After optimization of induction parameters to maximize yield of the His-tagged SUMO-SRC fusion protein in the soluble fraction, the recombinant protein will be purified by affinity chromatography over a nickel column. The activity of the recombinant protein will be determined in standard $\gamma$-$^{32}$P-ATP-based in vitro kinase assays using the peptide KYVVGYTGEGIKEVK (SEQ ID NO:1) as a substrate.

Determination of His-SUMO-SRC Activity in a Standard in-Gel Kinase Assay.

The extent to which the kinase activity of SUMO-SRC can be restored after denaturing PAGE will be determined. These experiments will serve as range finding studies to allow estimation the mass of SUMO-SRC required to perform a RIKA. That mass is a function not only of the intrinsic kinase activity of the recombinant protein, but also by the proportion that can be correctly refolded after denaturing gel electrophoresis. To generate a SRC substrate-containing gel, the peptide KYVVGYTGEGIKEVK (SEQ ID NO:1) will be covalently crosslinked to poly-Lys-Trp. A titration of SUMO-SRC spanning at least two orders of magnitude will be electrophoresed on the substrate-containing gel, and a standard in-gel kinase will then be performed. Based on the results of these experiments we will design a RIKA for the SUMO-SRC fusion protein.

Development of a 1D RIKA for SUMO-SRC.

To perform a 1D SUMO-SRC RIKA, a 16% polyacrylamide gel containing SUMO-SRC will be cast. A titration of the 1.6 kDa SRC substrate peptide KYVVGYTGEGIKEVK (SEQ ID NO:1) covering several orders of magnitude will be electrophoresed through the SUMO-SRC containing gel. After SDS removal, in-gel refolding, and a kinase reaction an autoradiogram of the dried RIKA gel will be obtained. The limit of detection for the peptide substrate will be determined based on the point in the titration where signal can no longer be distinguished above background.

Development of a 2D RIKA for SUMO-SRC.

Although SRC substrates have been identified in a variety of cells, a preponderance have been discovered in fibroblasts. Initially profile substrates of SUMO-SRC in extracts of NIH 3T3 fibroblasts will be determined. The overall strategy will follow that outlined above in 1a for CK22$\alpha$. 300 µg aliquots of cytoplasmic extracts from 3T3 cells prepared in the presence of protease and phosphatase inhibitors will be focused on 18 cm IPG strips and resolved on a second dimension gel containing SUMO-SRC. Autoradiograms of dried RIKA gels will be obtained to reveal the location of potential c-SRC substrates. LC-MS/MS analysis will be used to identify potential c-SRC substrates revealed by RIKA.

Exemplary embodiments of the present invention have been presented. The invention is not limited to these examples. These examples are presented herein for purposes of illustration, and not limitation. Alternatives (including equivalents, extensions, variations, deviations, etc., of those described herein) will be apparent to persons skilled in the relevant art(s) based on the teachings contained herein. Such alternatives fall within the scope and spirit of the invention.

All publications, patents and patent applications mentioned in this specification are herein incorporated by reference to the same extent as if each individual publication, patent or patent application was specifically and individually indicated to be incorporated by reference.

What is claimed is:

1. A method for identifying an inhibitor of enzyme activity, comprising:
   (a) providing a first and a second separation gel, each of which comprises at least one inactive enzyme that is capable of modifying at least one protein, wherein the at least one inactive enzyme is uniformly immobilized within each of the separation gels, and wherein the inactive enzyme is capable of re-activation;
   (b) loading a collection of macromolecules comprising at least one enzyme substrate into the first and the second protein separation gels to generate loaded separation gels;
   (c) resolving the at least one enzyme substrate on the first and second loaded separation gels to generate resolved separation gels;
   (d) washing the resolved separation gels;
   (e) incubating the first and second resolved separation gels in a protein re-activating buffer to re-activate the inactive enzyme;
   (f) incubating the first resolved separation gel in an enzyme reaction buffer;
   (g) incubating the second resolved separation gel in an enzyme reaction buffer that further comprises at least one potential inhibitor of enzyme activity; and
   (h) detecting at least one enzyme substrate in the first resolved separation gel and the second resolved separation gel;
   (i) comparing the first resolved separation gel and the second resolved separation gel, wherein a reduction in the detection of at least one enzyme substrate in the second resolved separation gel indicates that enzyme activity has been inhibited; and
   (j) identifying at least one inhibitor of enzyme activity.

2. The method of claim 1, wherein said providing comprises providing a first and second separation gel, each comprising at least one inactive kinase, wherein the at least one inactive kinase is uniformly immobilized within the separation gels.

3. The method of claim 1, wherein the enzyme reaction buffer comprises an enzyme substrate label.

4. The method of claim 3, wherein said enzyme reaction buffer comprises a radioactive enzyme substrate label, a fluorescent enzyme substrate label, a luminescent enzyme substrate label or a calorimetric enzyme substrate label.

5. The method of claim 4, wherein said enzyme reaction buffer comprises a radioactive enzyme substrate label.

6. The method of claim 1, further comprising labeling the at least one enzyme substrate.

7. The method of claim 6, wherein said labeling comprises labeling the enzyme substrate with a radioactive enzyme substrate label, a fluorescent enzyme substrate label, a luminescent enzyme substrate label or a colorimetric enzyme substrate label.

8. The method of claim 7, wherein said labeling comprises labeling the enzyme substrate with a radioactive enzyme substrate label.

9. The method of claim 1, wherein said resolving comprises separating the at least one enzyme substrate in the first and second loaded separation gels using electrophoresis.

10. The method of claim 1, wherein said resolving comprises focusing the at least one enzyme substrate in the first and second loaded separation gels using a pH gradient.

11. The method of claim 1, wherein said resolving comprises focusing the at least one enzyme substrate on the first and second loaded separation gels using a pH gradient and separating the at least one enzyme substrate on the first and second loaded separation gels using electrophoresis.

12. The method of claim 5 or claim 8, wherein said detecting comprises exposing a detection medium to the radioactively labeled enzyme substrate.

13. The method of claim 12, wherein said detecting comprises exposing an X-ray film to the radioactively labeled enzyme substrate.

14. A method for identifying an inhibitor of enzyme activity, comprising:
  (a) providing a separation gel which comprises at least one inactive enzyme that is capable of modifying at least one protein, and at least substrate for the enzyme, wherein the at least one enzyme and the at least one inactive enzyme substrate are uniformly immobilized within the separation gel, and wherein the enzyme is capable of re-activation
  (b) loading a collection of macromolecules comprising at least one potential inhibitor of enzyme activity into the separation gel to generate a loaded separation gel;
  (c) resolving at least one potential inhibitor of enzyme activity on the loaded separation gel to generate a resolved separation gel;
  (d) washing the resolved separation gel;
  (e) incubating the resolved separation gel in a protein re-activating buffer to re-activate the inactive enzyme;
  (f) incubating the resolved separation gel in an enzyme reaction buffer;
  (g) detecting at least one enzyme substrate in the resolved separation gel;
  (h) comparing a first portion of the resolved separation gel and a second portion of resolved separation gel, wherein a localized reduction in the detection of at least one enzyme substrate in the first portion compared to the second portion indicates that enzyme activity has been inhibited; and
  (i) identifying the inhibitor of enzyme activity.

15. The method of claim 14, wherein said providing comprises providing a separation gel comprising at least one inactive kinase, wherein the at least one inactive kinase is uniformly immobilized within the separation gel.

16. The method of claim 14, wherein the enzyme reaction buffer comprises an enzyme substrate label.

17. The method of claim 16, wherein said enzyme reaction buffer comprises a radioactive enzyme substrate label, a fluorescent enzyme substrate label, a luminescent enzyme substrate label or a colorimetric enzyme substrate label.

18. The method of claim 17, wherein said enzyme reaction buffer comprises a radioactive enzyme substrate label.

19. The method of claim 14, further comprising labeling the at least one enzyme substrate.

20. The method of claim 19, wherein said labeling comprises labeling the enzyme substrate with a radioactive enzyme substrate label, a fluorescent enzyme substrate label, a luminescent enzyme substrate label or a colorimetric enzyme substrate label.

21. The method of claim 20, wherein said labeling comprises labeling the enzyme substrate with a radioactive enzyme substrate label.

22. The method of claim 14, wherein said resolving comprises separating the at least one inhibitor on the loaded separation gel using electrophoresis.

23. The method of claim 14, wherein said resolving comprises focusing the at least one inhibitor on the loaded separation gel using a pH gradient.

24. The method of claim 14, wherein said resolving comprises focusing the at least one inhibitor on the loaded separation gel using a pH gradient and separating the at least one inhibitor on the loaded separation gel using electrophoresis.

25. The method of claim 18 or claim 21, wherein said detecting comprises exposing a detection medium to the radioactively labeled enzyme substrate.

26. The method of claim 25, wherein said detecting comprises exposing an X-ray film to the radioactively labeled enzyme substrate.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Lys Tyr Val Val Gly Tyr Thr Gly Glu Gly Ile Lys Glu Val Lys
1               5                   10                  15
```